Figure 1:
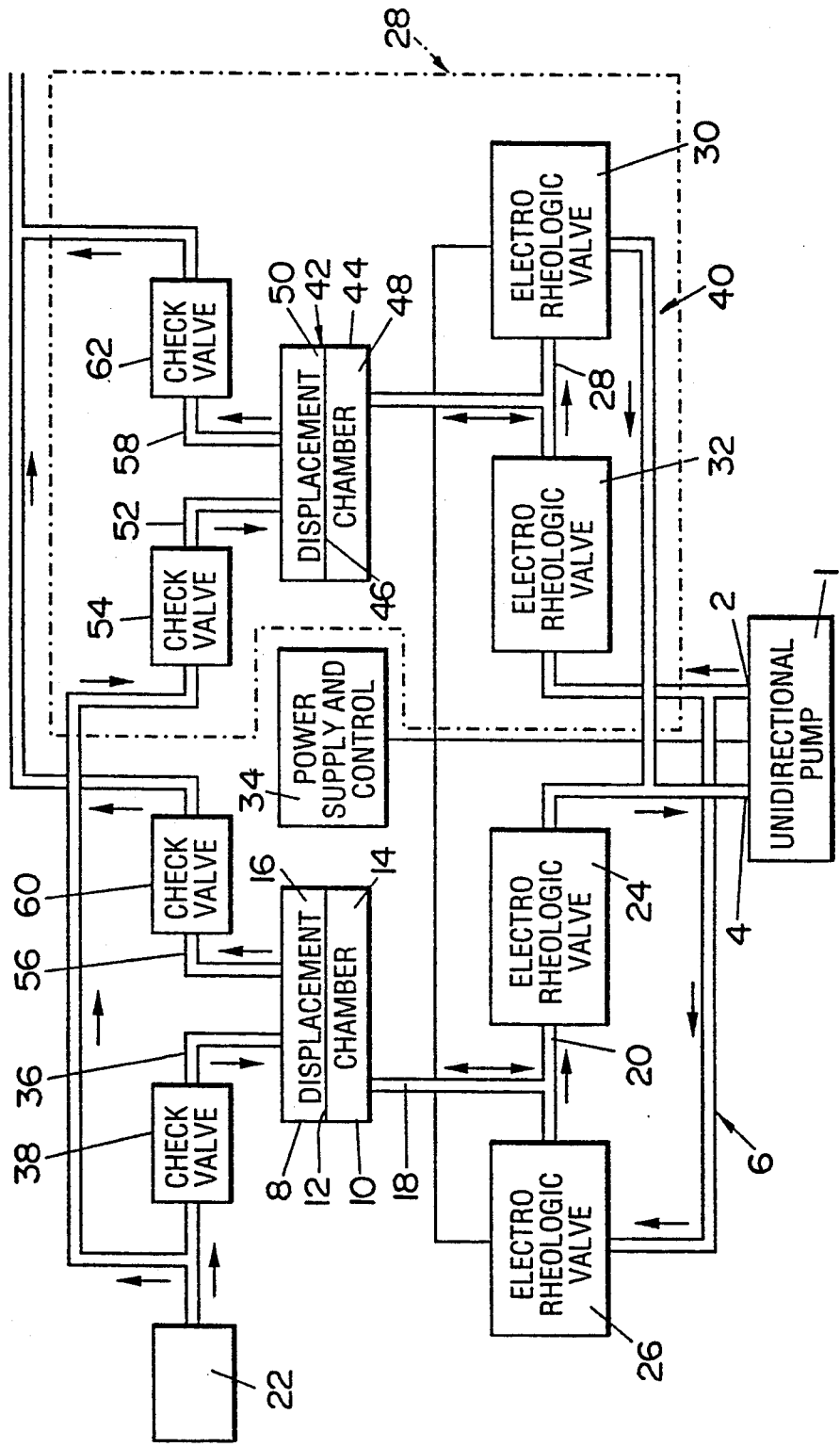

United States Patent [19]

Hayes et al.

[11] Patent Number: 5,269,811
[45] Date of Patent: Dec. 14, 1993

[54] PRIMARY FLUID ACTUATED, SECONDARY FLUID PROPELLING SYSTEM

[75] Inventors: William F. Hayes, Gloucester; John W. Tanney, deceased, Nepean, both of Canada, by Dorothy Tanney, legal representative

[73] Assignee: National Research Council of Canada, Ottawa, Canada

[21] Appl. No.: 730,819

[22] PCT Filed: Nov. 26, 1990

[86] PCT No.: PCT/CA90/00417
§ 371 Date: Jul. 25, 1991
§ 102(e) Date: Jul. 25, 1991

[87] PCT Pub. No.: WO91/08003
PCT Pub. Date: Jun. 13, 1991

[30] Foreign Application Priority Data

Nov. 30, 1989 [CA] Canada ................................ 2004295

[51] Int. Cl.⁵ ............................................. A61M 1/12
[52] U.S. Cl. ............................................. 623/3; 600/16;
417/48; 417/395; 623/24; 623/26
[58] Field of Search ................... 623/3, 24, 26; 600/16, 600/17; 417/48, 395

[56] References Cited

U.S. PATENT DOCUMENTS

| | | | |
|---|---|---|---|
| 3,405,728 | 10/1968 | Dexter | 417/48 |
| 3,838,946 | 10/1974 | Schall | 417/395 |
| 3,885,251 | 5/1975 | Pedroso | 623/3 |
| 4,192,293 | 3/1980 | Asrican | 600/17 |
| 4,381,567 | 5/1983 | Robinson et al. | 623/3 |
| 4,532,853 | 8/1985 | Stangroom | 137/807 X |
| 4,942,735 | 7/1990 | Mushika et al. | 60/416 |

FOREIGN PATENT DOCUMENTS 1511658  5/1978  United Kingdom ........... 137/596.16

Primary Examiner—Randall L. Green
Assistant Examiner—D. Willse
Attorney, Agent, or Firm—Marks & Clerk

[57] ABSTRACT

A primary fluid actuated, secondary fluid propelling system, suitable for use, for example, as an implantable, artificial heart device, comprises a unidirectional pump for pumping electrorheological fluid, two return loops connected to the pump, and for each return loop, two electrorheological valves therein in series flow, and a primary fluid actuated, secondary fluid propelling device connected to that loop at a position between the two electrorheologocal valves therein. The primary fluid actuated, secondary fluid propelling devices may comprise a casing having the interior thereof divided by a pressure transmitting flexible diaphragm into a first cavity for receiving electrorheological fluid from that return loop, and a second cavity for propelling the secondary fluid. The electrorheological valves are actuated to pressurize one first cavity while emptying the other and vice versa. In heart assist pump embodiments of the present invention, the primary fluid actuated, secondary fluid propelling device is replaced by, for example, a flexible container for placement in the body cavity for in operation, transmitting fluid pressure within the cavity.

10 Claims, 10 Drawing Sheets

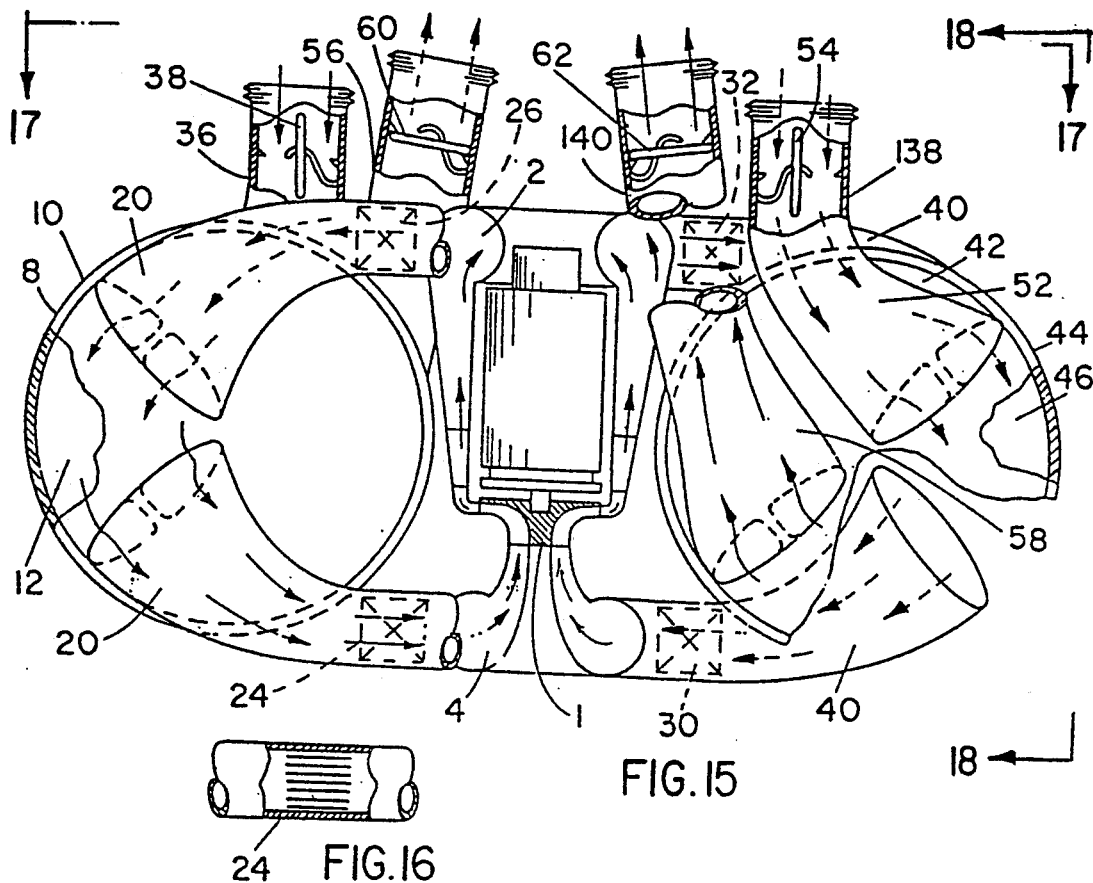
FIG. 15
FIG. 16
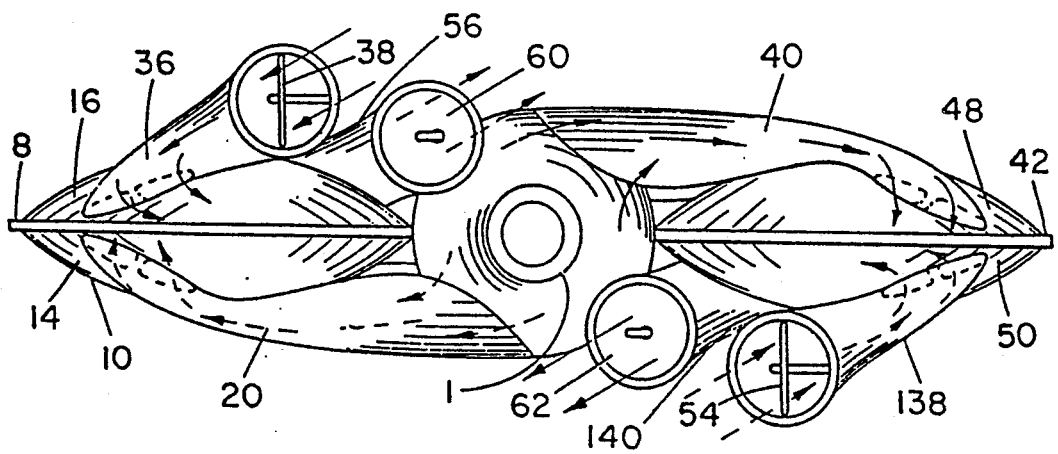
FIG. 17

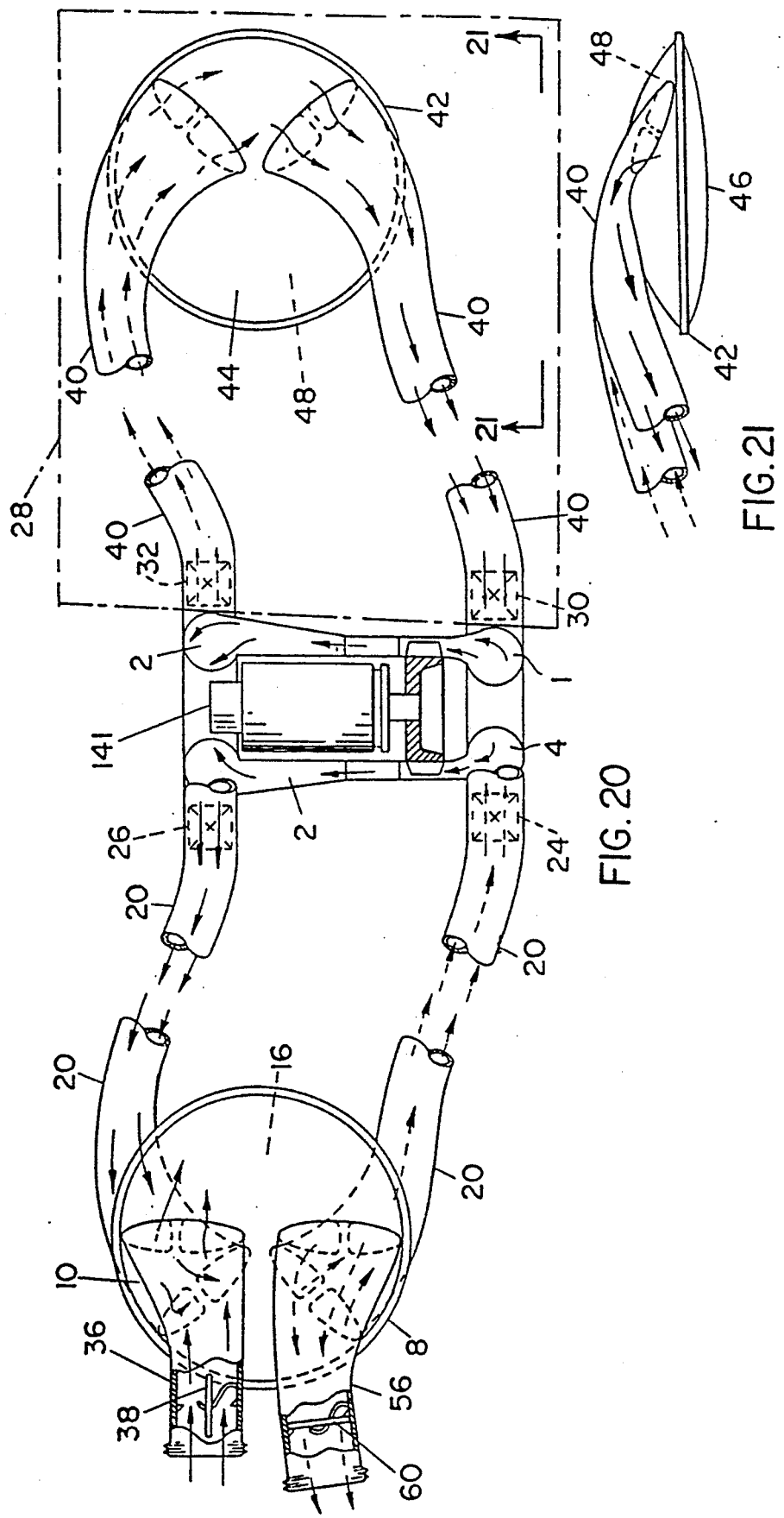

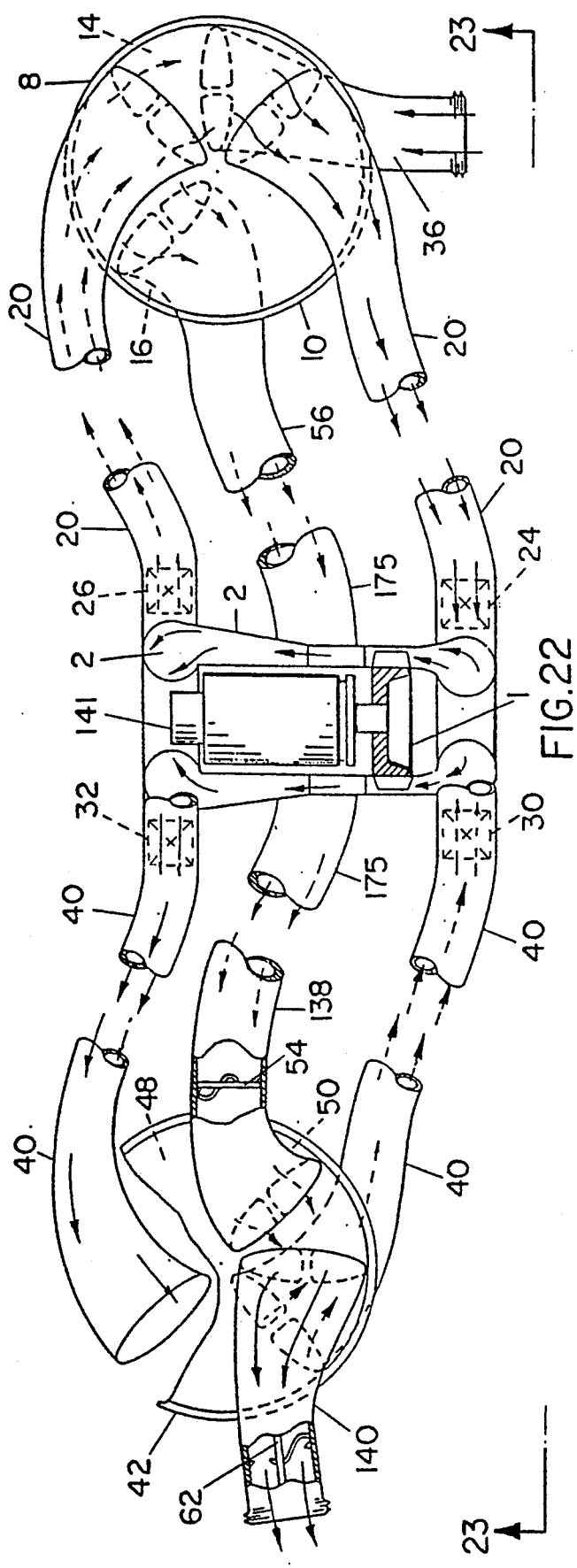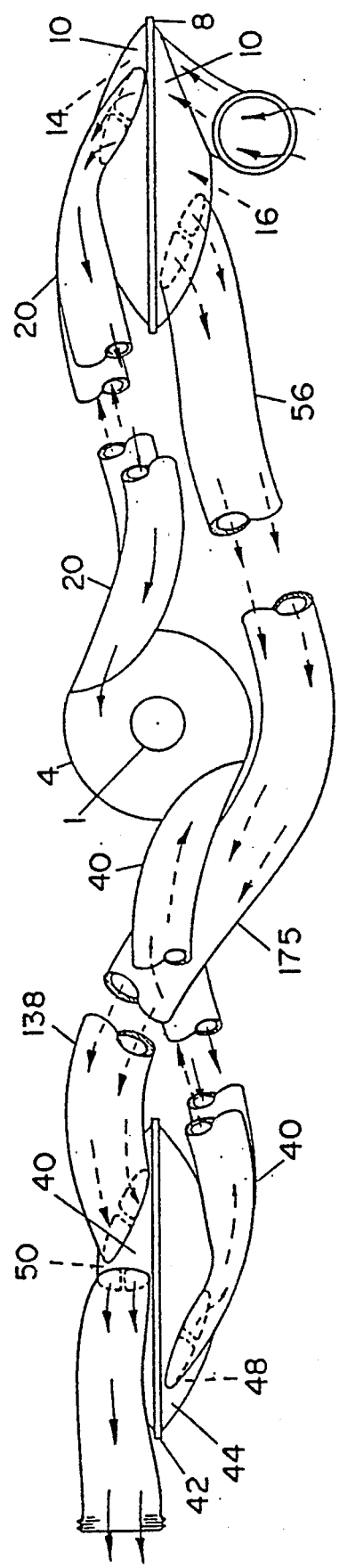

PRIMARY FLUID ACTUATED, SECONDARY FLUID PROPELLING SYSTEM

This invention relates to a primary fluid actuated, secondary fluid propelling system.

There are applications in the pumping of fluids where direct contact between the pumped fluid and parts of the pumping apparatus are undesirable for reasons of adverse effects upon the fluid exposed parts of the pumping apparatus by a particular fluid, such as the corrosion or erosion of pumping parts, or upon the pumped fluid, such as the physical alteration of the fluid under the impact and shearing action of active rotary or reciprocating fluid pumping devices. It is advantageous in such applications to isolate the pumped fluid from direct exposure to such portions of the pumping apparatus which would otherwise be damaged or caused to malfunction by the fluid, or would cause damage to, or otherwise adversely alter, the pumped fluid.

Examples of such applications are the pumping of highly caustic fluids which could damage the pumping apparatus and the pumping of blood which could be adversely altered by the action of the pumping apparatus. Typically with such applications, the pumped fluid is isolated from most of the parts of the pumping apparatus and in particular from such active high speed rotary or reciprocating parts by means of a flexible diaphragm type of interface where this interface is designed to be substantially unaffected by or to cause no significant alteration to the pumped fluid. Many such diaphragm interfaced pump types are commercially available to meet specialized market needs.

The appropriate fluid flow circuit interconnections of the diaphragm interfaced pump chamber(s) and unidirectional flow check valves typically provides the desired fluid, pumping action where the diaphragm interface is cyclically displaced by suitable mechanical, electro-mechanical or, in particular instances, hydraulic fluid means. Hydraulic fluid actuation means for the pump diaphragm is particularly appropriate in the prevention of diaphragm stress concentrations and accordingly in the avoidance of premature diaphragm failure which may be induced by the non-uniform application of force over the diaphragm surface area as is frequently encountered with mechanically displaced diaphragms.

In particular applications of fluid pumps incorporating diaphragm interface(s) between the pumped fluid and the hydraulic actuation means for diaphragm displacement, there is the need for a device having a high degree of operational reliability with minimal preventative maintenance over an extended life span combined with high overall energy efficiency.

Such a need is particularly prominent, for example, in a pumping device applied for use with a human implantable cardiac assist device or with an implantable total artificial heart device. Typically, portable implanted artificial heart and cardiac assist devices are comprised of:

- an electro-mechanical, electro-mechanical-hydraulic or electro-magnetic blood pumping means appropriately interconnected surgically to the body vascular system,
- a electro-electronic sensory and control system for the appropriate operational regulation of the blood pumping means in response to sensed physiological and pumping means derived input signals,
- a limited capacity implanted high performance battery power supply for short-term operation of the blood pumping means,
- an inductive energy transmission means for transcutaneous power transfer from an external power supply,
- an external power supply source typically comprised of a high performance power pack worn by the patient for unrestricted mobility mode operation and comprised of a portable electric ac/dc power converter pack worn by the patient and cable connected to any suitable non-portable power supply for limited mobility mode operation.

In the case of such implantable cardiac assist and total artificial heart device blood pumping applications, the opportunity for in-situ device preventative maintenance without surgical intervention is typically severely restricted or non-existent for the implantation duration which can be as long as years while the pumping operational energy efficiency is of paramount importance to minimizing the power which is required to be inductively transferred to the implanted device. Hydraulic actuated artificial heart and heart assist devices have been disclosed, for example, in U.S. Pat. No. 4,173,796, dated Nov. 13, 1979, Robert K. Jarvik, assigned to the University of Utah, and have been fabricated for prototype testing purposes, see for example the reversible axial pump hydraulic artificial heart device which is under development by the University of Utah and the solenoid actuated sleeve valve unidirectional pump hydraulic artificial heart which is under development by Abiomed Incorp., 33 Cherry Hill Drive, Danvers, Mass., 01923.

Long-term implantable artificial heart and cardiac assist devices must be performance and otherwise acceptable in six major areas which are identified by Jarvik in U.S. Pat. No. 4,173,796, dated Nov. 13, 1979, as;

hematologically acceptable with respect to blood thrombus and red blood cell damage, nonobstructive to the pulmonary system, implantation safe with respect to anatomical fit and pressure or temperature induced local tissue or blood damage, operational reliability and durability, energy efficiency, psychological acceptability with respect to size, weight, noise and vibration, and cost.

There is a need to improve the reliability and the efficiency, and reduce the noise and the vibration of permanently implantable artificial heart and cardiac assist devices relative to known devices, and to avoid mechanical complexity.

Exceptional reliability of permanently implanted artificial heart apparatus and cardiac assist devices is an essential feature since any operational failure of an implanted total artificial heart apparatus would necessitate immediate massive medical intervention to prevent a fatality while any operational failure of an implanted cardiac assist device could potentially render the patient medically at risk depending on the extent of the natural heart deficiency and would probably require near term surgical intervention to facilitate correction of the device malfunction.

The durability of permanently implanted artificial heart apparatus and cardiac assist devices is important since detectable device wear out probably would necessitate periodic surgical intervention to facilitate maintenance procedures.

The energy efficiency of permanently implanted artificial heart apparatus and cardiac assist devices is important with respect to acceptable implanted battery power supply and portable external battery power supply weight and volume as well as to the size and heat dissipating dependent power rating of the body external to internal inductive power supply transfer device.

According to the present invention there is provided a primary fluid actuated, secondary fluid propelling system, comprising:
1) a unidirectional pump for, in operation, being flooded with electrorheological fluid, and having an outlet and an inlet,
2) a return loop connected for, in operation, being filled with electrorheological fluid, and conveying an electrorheological primary fluid from the pump outlet to the pump inlet,
3) a primary fluid actuated, secondary fluid propelling device, the propelling device comprising a casing and a fluid pressure transmitting device dividing the casing interior in a fluid tight manner into a first cavity and a second cavity, the first cavity being, in operation, filled with electrorheological fluid, and being connected to an intermediate, lengthwise extending portion of the return loop for, in operation, receiving therefrom pressurized, electrorheological primary fluid and then being partially evacuated of electrorheological primary fluid thereby, and the second cavity for, in operation, propelling secondary fluid from a source thereof,
4) an upstream electrorheological valve in an upstream portion of the return loop to the connection to the first cavity,
5) a downstream electrorheological valve in a downstream portion of the return loop from the connection to the first cavity,
6) a rheological fluid supplying/receiving means, comprising;
   i) an electrorheological supply valve for, in operation, supplying and receiving electrorheological fluid to and from the pump inlet, and
   ii) an electrorheological return valve for receiving electrorheological fluid from the pump outlet, and
7) an electrical control for energizing the electrorheological valves for, in operation, simultaneously allowing the flow of electrorheological fluid through the downstream valve and the supply valve, while substantially inhibiting the flow of electrorheological fluid through the upstream valve and the return valve, and vice versa.

In some embodiments of the present invention, the return loop is a first return loop, the return loop electrorheological valves are first return loop electrorheological valves, the fluid propelling device is a first fluid propelling device, and the source of rheological fluid further comprises;
1) a second return loop, in operation, filled with electrorheological fluid, and containing the electrorheological supply and return valves as second return loop electrorheological valves, and forming the connections between them and the pump inlet and outlet, and
2) a second fluid propelling device comprising a casing, and a fluid pressure transmitting device dividing the casing interior in a fluid tight manner into a first cavity, in operation, filled with electrorheological fluid, and connected to an intermediate, lengthwise extending portion of the second return loop having the return valve downstream, and the supply valve upstream, and a second cavity for, in operation, propelling secondary fluid.

In other embodiments of the present invention, the intermediate lengthwise extending portions of the first and second return loops are T-junctions with the crossbars of each T connected to the electrorheological valves, and the trunks of each T connected to fluid pressure transmitting devices.

The fluid pressure transmitting devices may each comprise a flexible diaphragm.

Central portions of the diaphragms may be stiffened, and a connecting rod is provided connecting the diaphragms and extending through the second cavities and the walls of the casings in a slidable, fluid tight manner.

A throttle may be provided between the second cavities.

The unidirectional pump is preferably an impeller pump.

The system may be shaped for an anatomical fit for the purpose of an implantable artificial heart pump.

In other embodiments of the present invention, the system is shaped for an anatomical fit for the purpose of an implantable artificial ventricle heart assist pump, and the electrorheological fluid supplying/receiving means further comprises a casing connected in series flow between the supply and return valves, and for, in operation, placement in the body cavity, at least a portion of the casing being flexible for, in operation, transmitting the body fluid pressure within the body cavity.

In other embodiments of the present invention, the system is shaped for an anatomical fit for the purpose of an implantable artificial ventricle heart assist pump, and the electrorheological fluid supplying/receiving means further comprises a substantially rigid casing, and a fluid pressure transmitting device dividing the casing interior into two cavities, one cavity within the casing being connected in series flow between the electrorheological fluid supply and return valves, and the other cavity within the casing being for in operation connection in series flow to the body blood stream.

Figure 2:
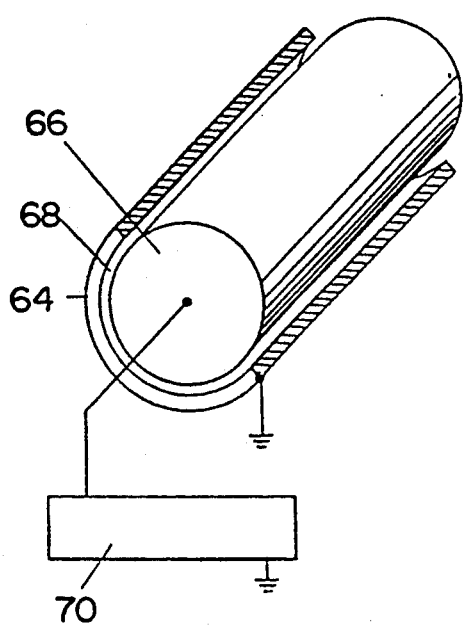

In the accompanying drawings which illustrate, by way of example, embodiments of the present invention;

FIG. 1 is a block diagram of a primary fluid actuated, secondary fluid propelling system, FIG. 2 is a partly sectioned, isometric view of a lengthwise extending portion of a prior art electrorheological valve with a portion of outer shell removed to reveal the inner electrode.

Figure 3:
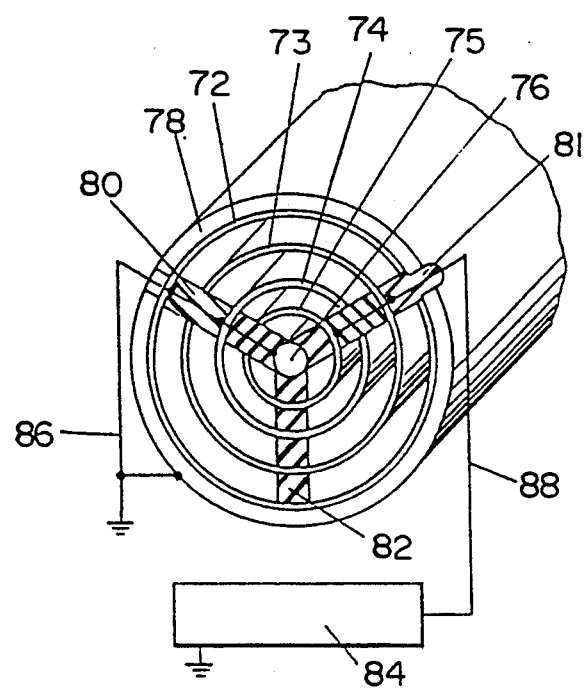
Figure 4:
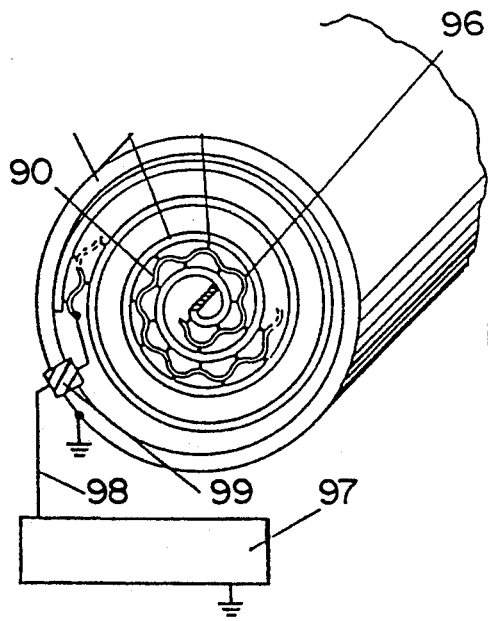
Figure 5:
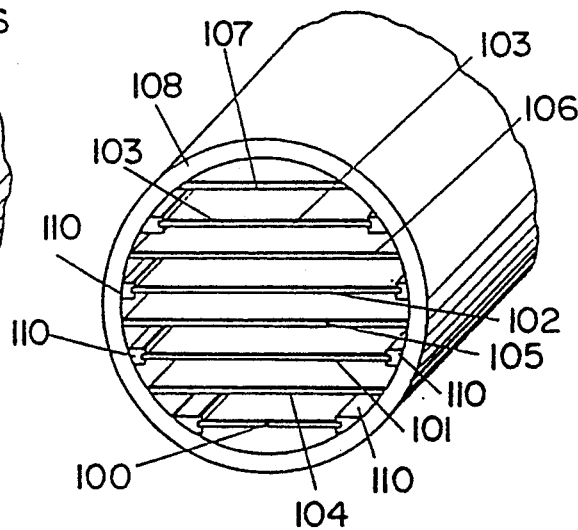
Figure 6:
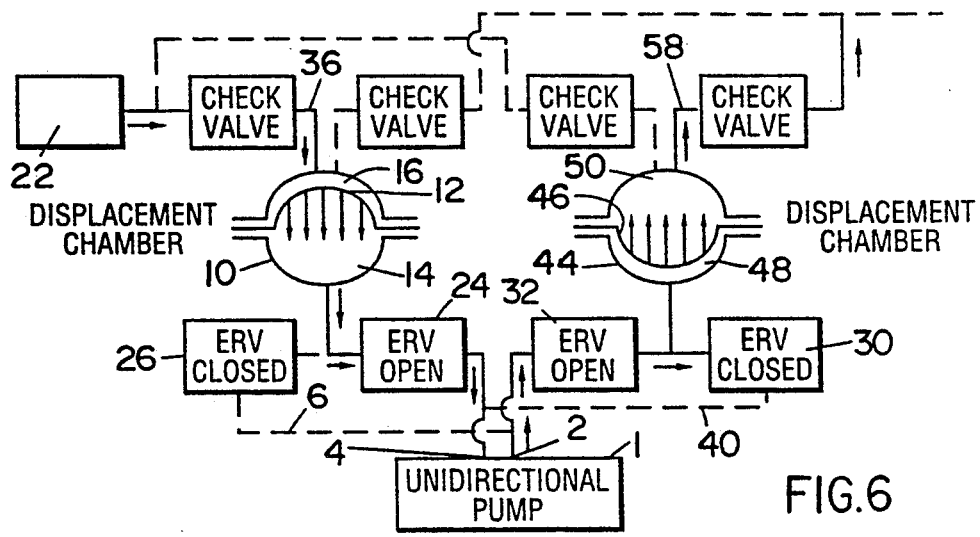
Figure 7:
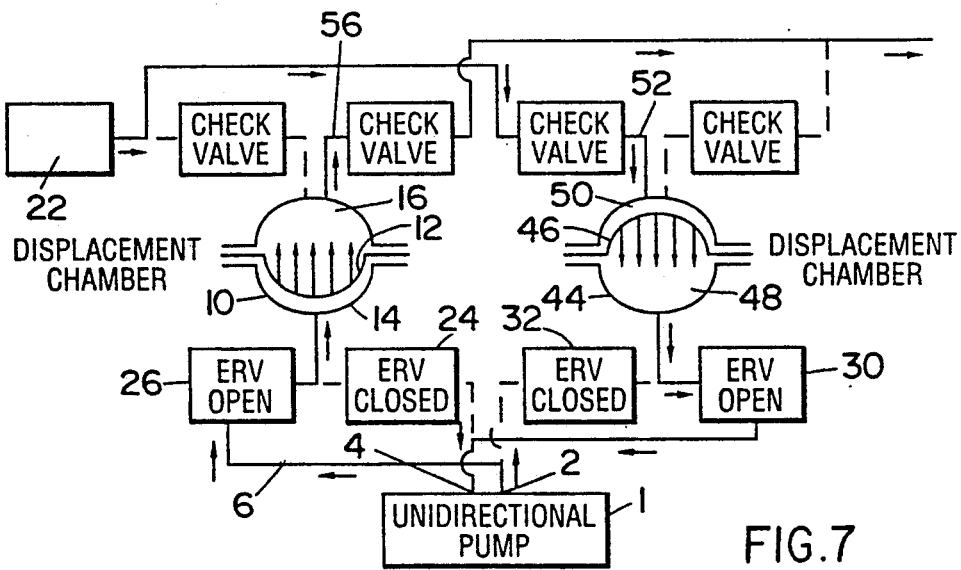
Figure 8:
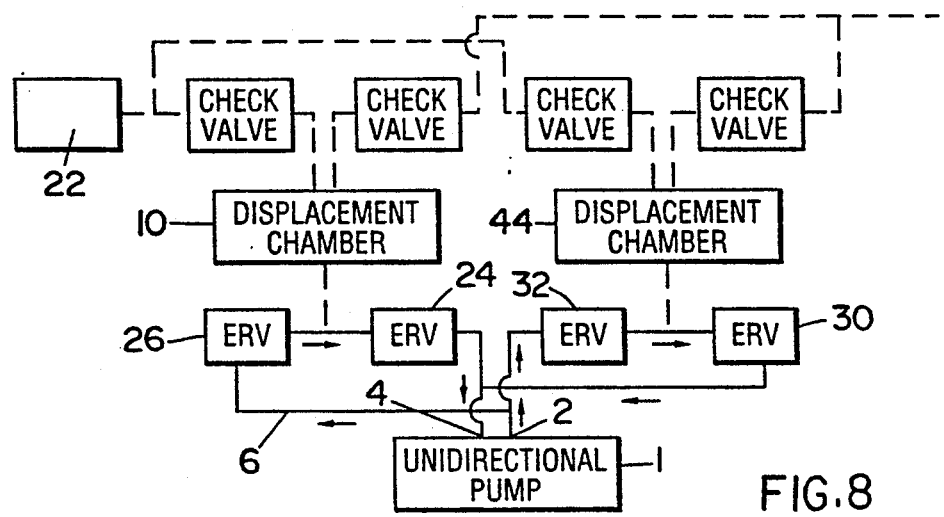
Figure 9:
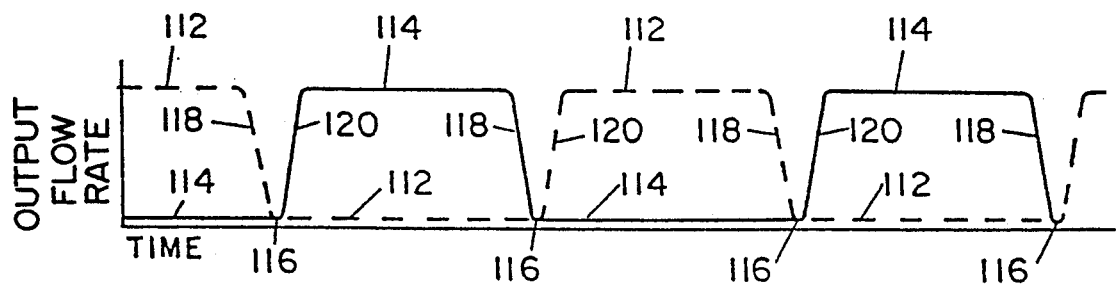
Figure 11:
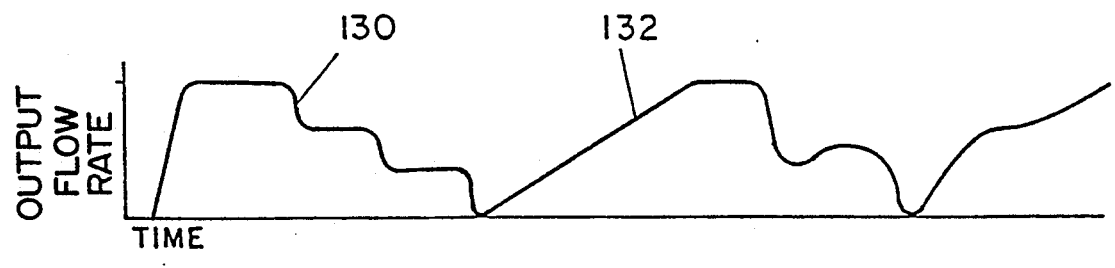
Figure 12:
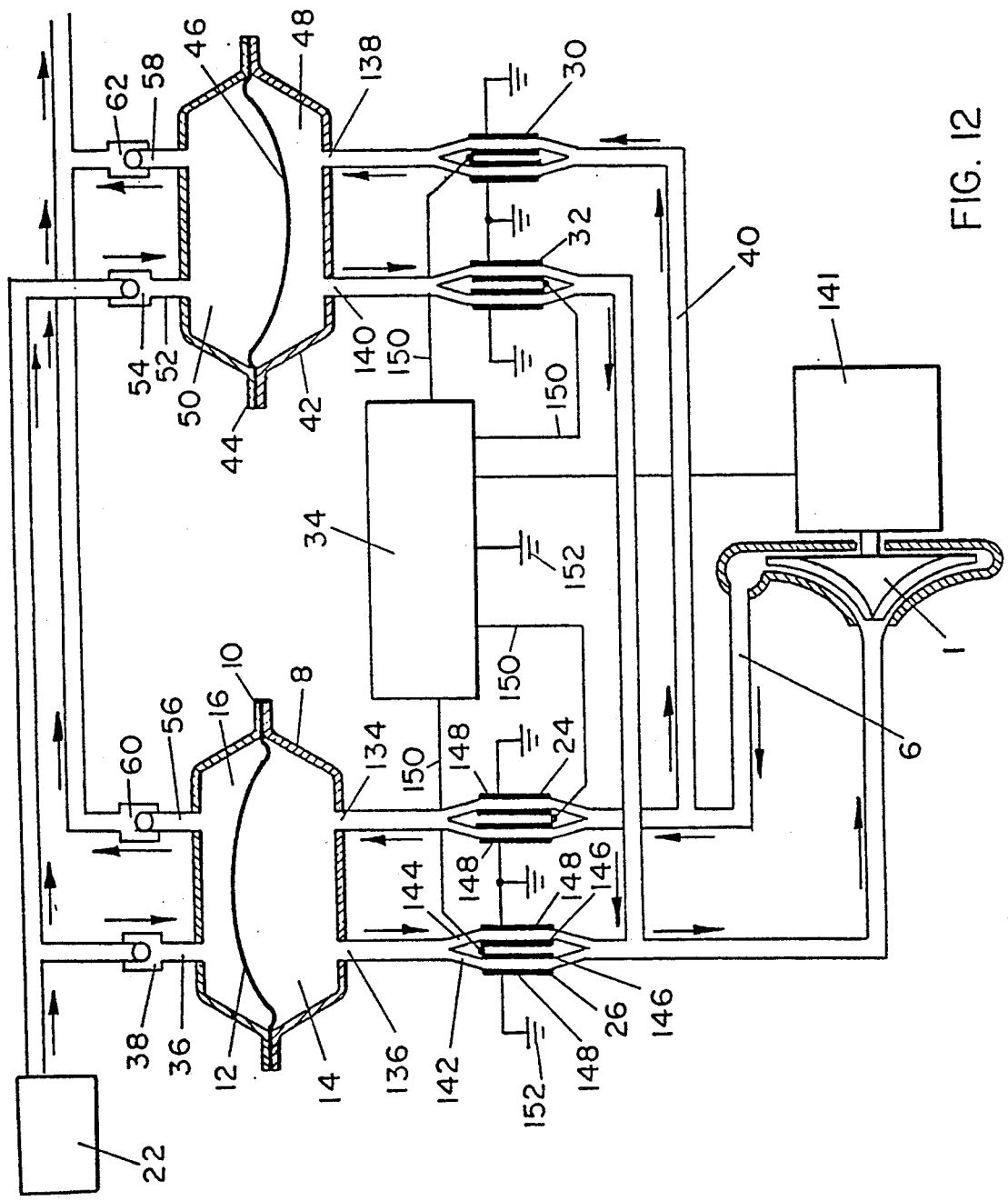
Figure 13:
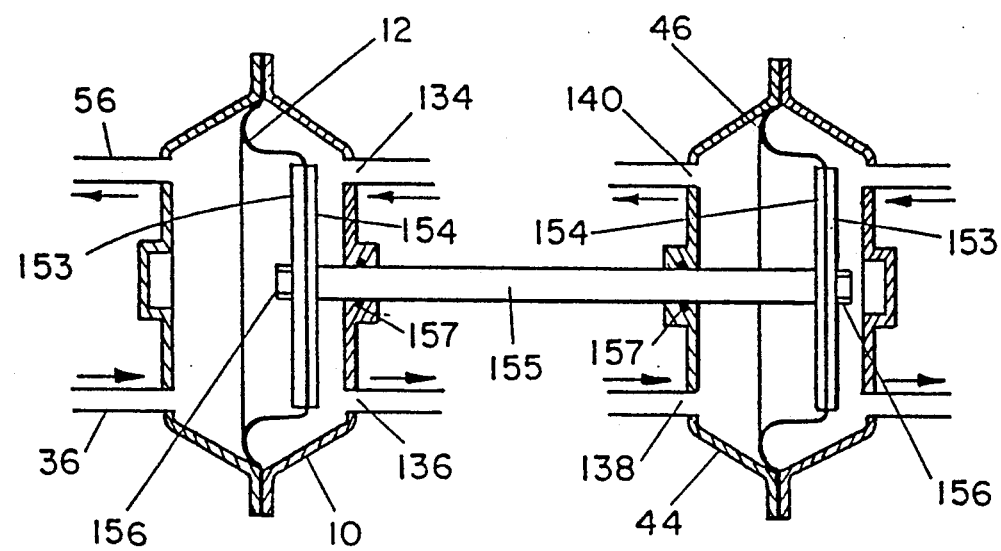
Figure 14:
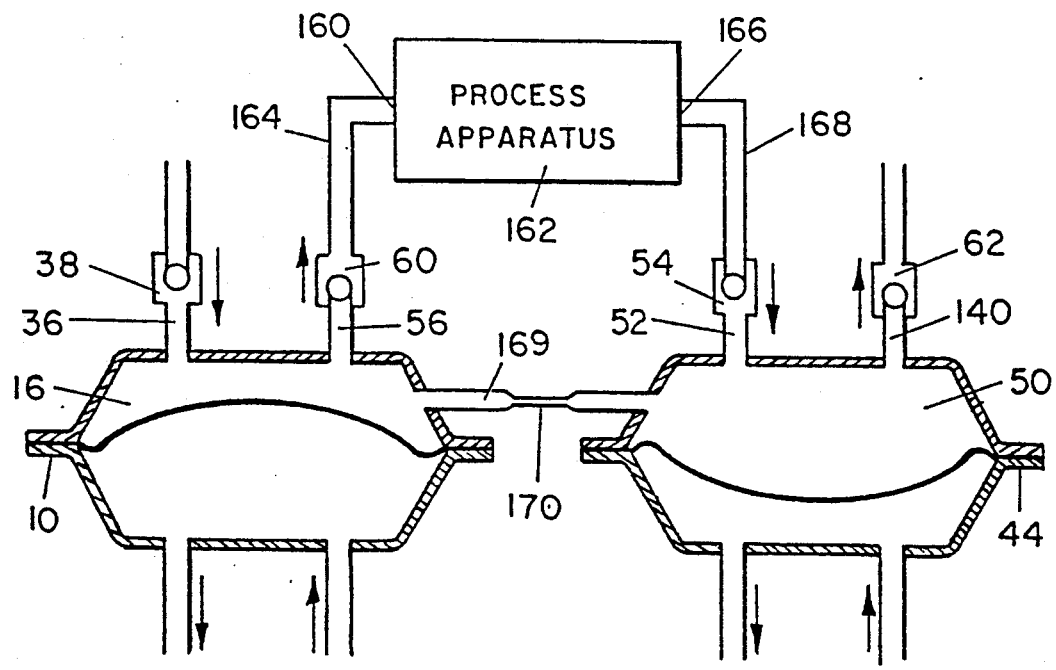
Figure 18:
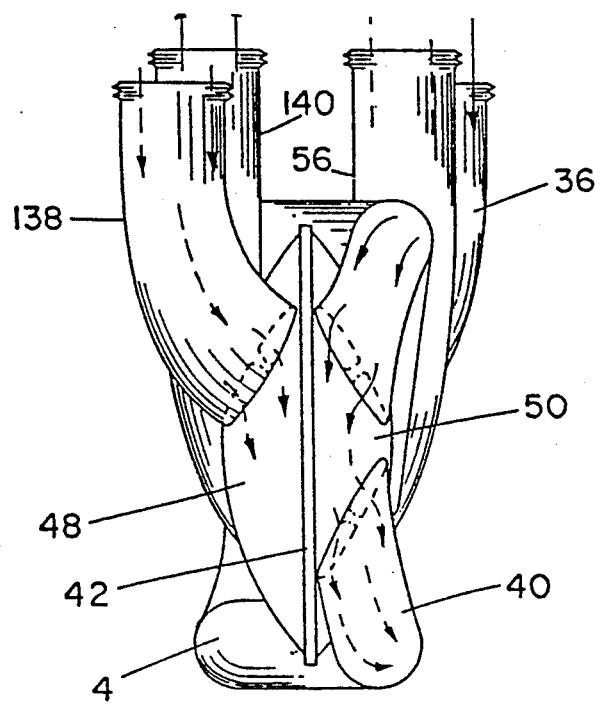
Figure 19:
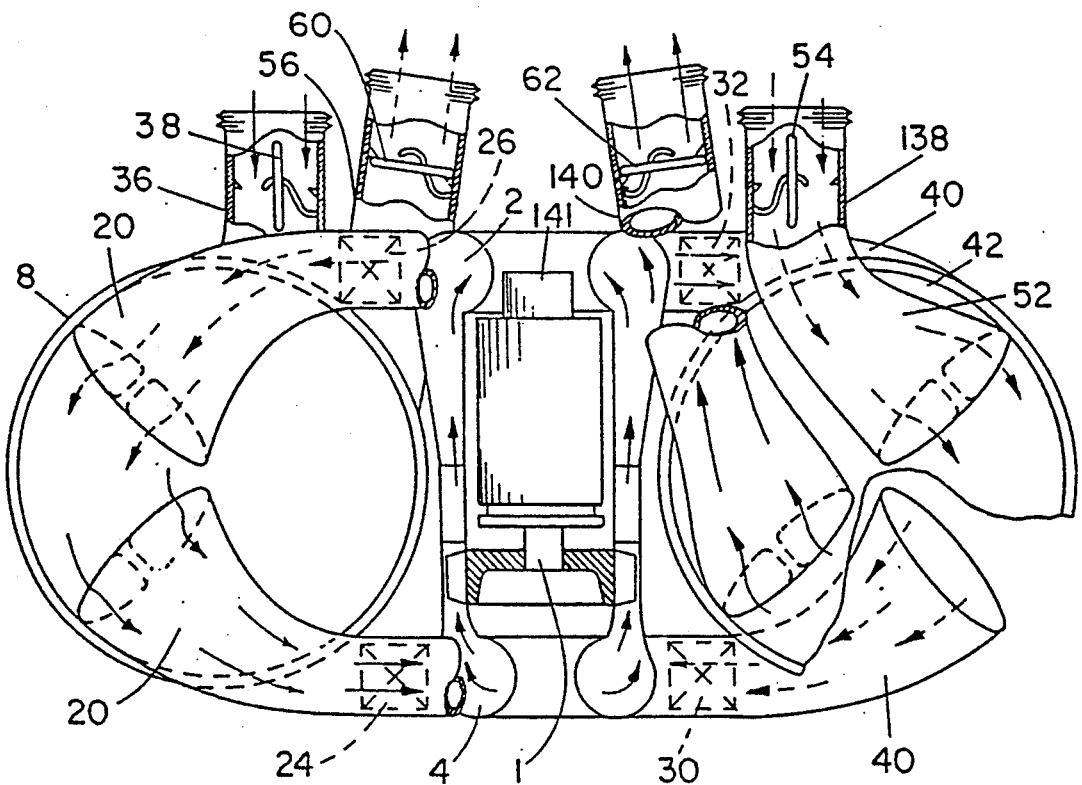

FIG. 3 is an isometric view of a lengthwise extending portion of a prior art electrorheological valve having multiple hollow cylindrical electrodes, FIG. 4 is an isometric view of a lengthwise extending portion of a prior art electrorheological valve having electrodes formed into a scroll, FIG. 5 is an isometric view of a lengthwise extending portion of a prior art electrorheological valve having flat plate electrodes, FIGS. 6 to 8 are block diagrams of a primary fluid actuated, secondary fluid propelling apparatus, FIG. 9 is graph showing the maximum flow rate output waveform for the primary fluid actuated, secondary fluid propelling apparatus shown in FIGS. 6 to 8, FIG. 10 is a graph showing a time duration modulated flow rate output waveform for the primary fluid actuated, secondary fluid propelling apparatus shown in FIGS. 6 to 8, FIG. 11 is a graph of an amplitude modulated flow rate output waveform for the primary fluid actuated, secondary fluid propelling apparatus shown in FIG. 6 to 8, FIG. 12 is a schematic, partly sectioned diagram of a portion of a primary fluid actuated, secondary fluid propelling apparatus, FIG. 13 is a schematic, partly sectioned diagram of a primary fluid actuated, secondary fluid propelling apparatus having mechanically connected diaphragms, FIG. 14 is a schematic, partly sectioned diagram of a portion of a primary fluid actuated, secondary fluid propelling apparatus used with a process apparatus, FIG. 15 is a partially sectioned front view of an electrorheological fluid powered heart pump, FIG. 16 is an enlarged, partly sectioned front view of one of the electrorheological valves shown in dotted outline at four locations in FIG. 15, FIG. 17 is a top view along A—A, of FIG. 15, FIG. 18 is a side view along B—B, of FIG. 15, FIG. 19 is a partly sectioned front view of an electrorheological fluid powered heart pump having as axial flow pump, FIG. 20 is a partly sectioned front view of an electrorheological fluid powered heart ventricle assist pump with an electrorheological fluid accumulator, FIG. 21 is a side view along C—C, of FIG. 20, FIG. 22 is a partly sectioned front view of portions of an electrorheological fluid powered heart ventricle assist pump with a blood flow compensated, electrorheological fluid accumulator, FIG. 23 is a side view along D—D, of FIG. 22.

In FIG. 1 there is shown a primary fluid actuated, secondary fluid propelling system, comprising:

1) a unidirectional pump 1 for, in operation, being flooded with electrorheological fluid, and having an outlet 2 and an inlet 4, 2) a return loop, generally designated 6, connected for, in operation, being filled with electrorheological fluid, and conveying an electrorheological primary fluid from the pump outlet 2 to the pump inlet 4, 3) a primary fluid actuated, secondary fluid propelling device, generally designated 8, comprising a casing 10 and a fluid pressure transmitting device 12 dividing the casing interior in a fluid tight manner into a first cavity 14 and a second cavity 16, the first cavity 14 for, in operation, being filled with electrorheological fluid, and being connected by a T-connection trunk forming pipe connection 18 to an intermediate, lengthwise extending, T-connection cross-bar portion 20 of the return loop 6 for, in operation, receiving therefrom pressurized, electrorheological primary fluid and then being at least partially evacuated of electrorheological primary fluid thereby, and the second cavity 16 being for connection for, in operation, propelling secondary fluid from a source 22 thereof, 4) a downstream electrorheological valve 24 in an downstream portion of the return loop 6 to the connection 18 to the first cavity 14, 5) a upstream electrorheological valve 26 in a upstream portion of the return loop 6 from the connection 18 to the first cavity 14, 6) a electrorheological fluid supplying/receiving means, generally designated 28 for, in operation, supplying and receiving electrorheological fluid to and from the pump 1, comprising;

i) an electrorheological supply valve 30 for supplying electrorheological fluid to the pump inlet 4, and ii) an electrorheological return valve 32 for receiving electrorheological fluid from the pump outlet 2, and 7) an electrical control 34 for energizing the electrorheological valves 24, 26, 30 and 32 for, in operation, simultaneously allowing the flow of electrorheological fluid through the upstream value 26 and the supply valve 30, while substantially inhibiting the flow of electrorheological fluid through the downstream valve 24 and the return valve 32 and vice versa.

The second cavity 16 is connected to the fluid source 22 by a pipe 36 containing a valve 38.

In this embodiment of the present invention, the return loop 6 is a first return loop, the return loop electrorheological valves 24 and 26 are first return loop electrorheological valves, the fluid propelling device 8 is a first fluid propelling device, and the source of rheological fluid 28 further comprises;

1) a second return loop 40, in operation, filled with electrorheological fluid, and containing the electrorheological supply and return valves, 30 and 32 respectively, as second return loop electrorheological valves, and forming the connections between them and the pump inlet 4 and outlet 2, and 2) a second fluid propelling device, generally designated 42, comprising a casing 44 and a fluid pressure transmitting device 46 dividing the casing interior in a fluid tight manner into a first cavity 48, in operation, filled with electrorheological fluid and connected to an intermediate, lengthwise extending portion of the second return loop, generally designated 40, having the supply valve 30 downstream and the return valve 32 upstream, and a second cavity 50 for connection through the casing 44 for, in operation, propelling secondary fluid, from a source thereof which in this instance is source 22.

The second cavity 50 is connected to the fluid source 22 by a pipe 52 containing a valve 54.

The second cavities 16 and 50 have outlet pipes 56 and 58 respectively containing valves 60 and 62 respectively. All of the valves 38, 54, 60 and 62 are check or non-return valves.

In operation, the apparatus is arranged as shown with the fluid pressure transmitting devices 12 and 46 at mid-stroke, the unidirectional pump 1 flooded with electrorheological fluid which also fills the return loops 6 and 40 and the first cavities 14 and 48, the second cavities 16 and 50, and the pipes 36 and 52 are flooded with secondary fluid from the source 22.

The pump 1 is then actuated and the control 34 used to open and allow the flow of electrorheological fluid through the electrorheological valves 24 and 32 and close or substantially inhibit flow thereof through the electrorheological valves 26 and 30.

With the system actuated in this manner, the pump 1 will withdraw electrorheological fluid from the first cavity 14 and fill the first cavity 48 with that fluid. This will cause the second cavity 50 to propel secondary fluid through the pipe 58 while the second cavity 16 will induce secondary fluid to flow along the pipe 36 from the source 22, and into the second cavity 16.

When the fluid pressure transmitting device 12 has completed its stroke, the control 34 is used to open and allow flow of electrorheological fluid through the electrorheological valves 26 and 30 while closing or substantially inhibiting the flow thereof through the electrorheological valves 24 and 32.

With the system actuated in this manner, electrorheological fluid is pumped from the first cavity 48 to the first cavity 14, so that the second cavity 16 induces secondary fluid to flow from the source 22 while the second cavity 50 propels secondary fluid along the pipe 58.

Sequentially actuating the electrorheological valves 24, 32 and 26, 30 in this manner will cause secondary fluid to be induced to flow sequentially by both second cavities 16 and 50 from the source 22.

The fluid pressure transmitting devices 12 and 46 may, for example, be impermeable flexible diaphragms, corrugated or rolling bellows, movable pistons, pressure intensifiers, the boundary between two immiscible fluids or any other known interface means for displacing one fluid by other fluid without mixing or otherwise affect the electrorheological or pumped fluids.

The unidirectional pump 1 may be any known fluid pumping apparatus which is suitable with respect to flow rate, pressure, and ability to pump electrorheological fluids for a specific implementation of the present invention and which provides a substantially continuous output of pressurized fluid flow. Suitable unidirectional pumps types, for example, are centrifugal, vane, axial, reciprocating piston, gear and vane rotary pumps.

The return loops 6 and 40 may comprise any suitable tubing, piping, hose, fittings and connecting portions extending between and communicating with the first cavities 14 and 48 in the casings 10 and 44, the electrorheological valves 24, 26, 30 and 32 and the unidirectional pump 1, provided that the return loops 6 and 40 are suitable for the flow rate and pressure of the electrorheological fluid used in any particular embodiment of the present invention.

The check valves 38, 54, 60 and 62 may be any known valving apparatus which provide for the substantially free flow of fluid in one direction and substantially zero flow of fluid in the opposite direction. Typical examples of such valve types are ball, disk, swinging gate, bicuspid or tricuspid valves.

The pipes 36, 52, 56 and 58 may comprise any suitable tubing, piping, hose, fittings and internal passages within the casings 10 and 44 and the valves 38, 54 60 and 62 provided that they are suitable for the flow rate and pressure of the pumped fluid used in any particular embodiment of the present invention.

The electrorheological valves 24, 26, 30 and 32 may, for example, be similar to those taught in a number of publications including those taught by Dexter in U.S. Pat. No. 3,405,728, dated Oct. 15, 1968; Stangroom in U.S. Pat. No. 4,342,334, dated Aug. 1982; Nuber in U.K. Patent No. 935,827, dated Mar. 1965; Denizov in U.K. Patent No. 1,385,551, dated Feb. 1985; Bullough in U.K. Patent No. 1,511,658, dated May 1978; Stangroom in U.K. Patent No. 2,118,741, dated December 1981 and U.K. Patent No. 2,120,806, dated December 1983; Stangroom in Hydraulics and Pneumatics, Sept. 1966 PP 139-143.

A known electrorheological valve embodiment as described and shown by Dexter in U.S. Pat. No. 3,405,728 is shown in FIG. 2. In FIG. 2, a lengthwise extending portion of an electrically conducting conduit 64 contains an electrically conducting cylindrical body 66 which is concentrically and rigidly mounted within the conduit 64 and is electrically insulated therefrom by means not shown. A suitable annular gap 68 is provided between the inner cylindrical body 66 and the conduit 64 for the flow of electrorheological fluid therethrough. An electrical power supply 70, which may be energized to provide a suitable alternating voltage potential, a substantially fixed voltage potential, or a pulsed voltage potential, is connected across the cylindrical body 66 and the conduit 64.

In the operation, with the power supply 70 de-energized, an electrorheological fluid may flow freely through the gap 68 between the cylindrical body 66 and the conduit 64 without impediment except for that provided by the fluid flow drag induced by the boundary walls of the gap 68 when the power supply 70 is de-energized. However, energization of the power supply 70 produces an electrical field between the cylindrical body 66 and the conduit 64 which will induce a finite yield strength to the electrorheological fluid flowing within the gap 68 which will increase the apparent viscosity of the fluid when an externally applied fluid pressure load is greater than the induced fluid yield strength. Accordingly, for a fluid applied pressure load equal to or less than the electrorheological fluid yield strength, the valve may be closed by substantially inhibiting the flow of electrorheological fluid through the gap 68, by means of the application of an appropriate electrical field or voltage across the gap 68 by energizing the power supply 70. For a fluid applied pressure load greater than the electrorheological fluid yield strength, the fluid flow rate through the gap 68 may be regulated as a unique function of the electrical field or voltage applied across the gap 68.

Another known electrorheological valve embodiment as described and shown by Dexter in U.S. Pat. 3,405,728 is shown in FIG. 3. In FIG. 3, concentric and coaxially disposed hollow cylindrical, thin shell, electrically conducting electrodes 72 to 75 are radially spaced coaxially around a central, cylindrical, electrically conducting, solid electrode 76 and are contained within a conduit 78. The positions of the electrodes 72 to 75 are maintained by means of electrically insulating spacers 80 such that the spacing between any two adjacent electrodes 72 to 75 is substantially the same. Electrodes 72, 74 and 76 are electrically connected to the output of a suitable power supply 84 and electrodes 73 and 75 are connected to a corresponding but opposite polarity output of the power supply 84. An electrical lead 86 connects the electrodes 72, 74 and 76 through the radial spacer 80 which also functions as an insulating bushing from electrodes 73 and 75 while electrodes 73 and 75 are electrically connected by the lead 88 through radial spacer 81 which also functions as an insulating bushing through electrodes 72 and 74.

The operation of the apparatus shown in FIG. 3 is similar to that described with reference to FIG. 2 in that when the valve is de-energized, electrorheological fluid may flow through the gaps between the electrodes 72 to 76 without impediment except for that provided by the fluid flow drag induced by the boundary walls of these gaps and by the bushings 80 to 82. Energization of the valve by the power supply 84 will induce a finite yield strength in the electrorheological fluid flowing within the gaps and which additionally will increase the apparent viscosity of the fluid as has been described with reference to FIG. 2.

Another known electrorheological valve embodiment as described and shown by Dexter in U.S. Pat. 3,405,728 is shown in FIG. 4. In FIG. 4, the electrodes of the electrorheological valve comprise two spaced electrically conducting plate electrodes 90 and 92, wrapped to form a scroll and both electrodes are contained within a conduit 94. The electrode 90 is corrugated to follow an undulating path in a spiral direction between the coils of smooth electrode 92. Lines of contact or tangency between the corrugated electrode 90 and the smooth electrode 92 are made with an insulating material 96 to prevent any direct electrical connection between the electrodes 90 and 92. A power supply 97, similar to that described with reference to FIG. 2, is connected to the corrugated electrode 90 by means of a lead 98 through an electrically insulating bushing 99. A corresponding lead (not shown) of opposite polarity may extend from the power supply 97 to the smooth electrode 92 through a similar bushing or this electrode may be grounded by means of a common ground between the smooth electrode and the power supply 97. It will be appreciated that the electrode 90 need not be corrugated but may also be in the form of a smooth spiral with insulators being provided of an appropriate size and number to maintain a desired spacing between the electrodes 90 and 92 as taught by Dexter in U.S. Pat. No. 3,405,728.

The operation of the apparatus shown in FIG. 4 is similar to that described with reference to FIG. 2 in that when the valve is de-energized, the electrorheological fluid may flow through the gaps between the spirally wound electrodes 90 and 92 without impediment except that provided by the fluid flow drag induced by the walls bounding these gaps and by the insulations 96. Energization of the valve by the power supply 97 will induce a finite yield strength in an electrorheological fluid flowing within the gaps and additionally will increase the apparent viscosity of the said fluid when the externally applied fluid pressure load is greater than the induced fluid yield strength as has been described with reference to FIG. 2.

Another known electrorheological valve embodiment as described and shown by Dexter in U.S. Pat. No. 3,405,728 is shown in FIG. 5. In FIG. 5, the electrodes of an electoreological valve comprise a series of stacked and separated conducting flat plates 100 to 107 contained within a portion of an electrically conducting conduit 108 by insulators 110 and is connected to one output of a power supply (not shown) such as that described with reference to FIG. 2 and designated 70. The other set of alternate plates 104 to 107 is connected in an electrically conductive manner at their edges to the conduit 108 which is in turn connected to a corresponding but opposite polarity output of the power supply.

The apparatus shown in FIG. 5 is similar to that which is described by Stangroom in U.K. Patent No. 2,118,741, FIGS. 2 and 4, except that the fluid flow conduit shown and described in Stangroom is square in cross section.

The operation of the apparatus shown in FIG. 5 is similar to that described with reference to FIG. 2 in that when the valve is de-energized the electrorheological fluid may flow freely through the gaps between the flat plate electrodes 100 to 107 without impediment except that provided by the fluid flow drag induced by the boundary walls of the gaps and the insulators 110. Energization of the valve by the power supply will induce a finite yield strength in an electrorheological fluid flowing within the gaps between the flat plate electrodes 100 to 107 and additionally will increase the apparent viscosity of the said fluid when the externally applied fluid pressure load is greater than the induced fluid yield strength as has been described with reference to FIG. 2.

The electrorheological fluid is a two-phase fluid whose rheological properties may, as has been previously stated, be modified when an electric field is applied to electrorheological fluid. Electrorheological fluids may be in a dispersed phase, usually in the form of a finely ground powder in size ranging from 0.04 to 50. microns dispersed in a liquid dispersant, which is generally a high electrical resistance fluid and a controlled proportion of water as an addition to the two phase mixture. Many known additives, dispersed phases and dispersants may be used.

As previously stated, the electrorheological fluids will, under the influence of an applied electrical voltage field, increase in apparent viscosity in response to the strength of such voltage field and, when the strength of the applied field is sufficient, will exhibit a finite yield strength in a manner similar to a Bingham Plastic such that it will then substantially adhere to the surfaces of the electrodes providing the applied field. Electrorheological fluids, suitable for use in the present invention, will, as has been previously described, when used with appropriately energized electrorheological valves, become sufficiently rigid to completely block the flow of fluid through selected valves so as to redirect the output from, and the input to, the unidirectional pump. These fluids, which were first described by Winslow in U.S. Pat. No. 2,417,850, dated May, 1947, have been further described by Stangroom in U.S. Pat. Nos. 2,153,372, dated Aug. 1985; No. 2,170,510, dated Aug. 1986; and by Goosens in U.S. Pat. No. 4,645,614, dated Feb. 1987; No. 4,668,417, dated May 1987; No. 4,702,855, dated Oct. 1987 and are well known in the art.

An extensive review article on electrorheology has been published by H. Block and J.P. Kelly in Journal of Physics D: Applied Physics, Vol. 21 (1988) pp. 1661–1667. This paper, in Table 1, lists a wide range of dispersed materials, dispersants and additives that have, in various combinations, demonstrated electrorheological effects. This table, published with kind permission of the authors and publisher, is given as the following Table 1 to show examples of rheological fluids.

TABLE 1

| Dispersed Phase | The composition of ER-active fluid dispersions Dispersant | Additive |
|---|---|---|
| Alginic acid | Polycholorinated biphenyls, poly(tri-fluorovinyl chloride), o-dichlorobenzene, p-chlorotoluene, -xylene, plus mixtures of above | Water |
| Aluminum dihydrogen tripoly-phosphate | Mineral oil | Water |
| Aluminum oxide (as coating on aluminum) | Spindle oil or water | — |

TABLE 1-continued

The composition of ER-active fluid dispersions

| Dispersed Phase | Dispersant | Additive |
|---|---|---|
| Calcium titanate | Naphthenic oil | Non-ionic surfactant |
| Carbon | Transformer oil, olive oil or mineral oil | |
| (coal) | 'Heavy' oil | Water and surfactant |
| Carboxymethyl dextran | Polychlorinated biphenyls or poly(trifluorovinyl chloride), o-dichlorobenzene or xylene or mixtures of the above | Water and sorbitan mono-oleate or sorbitan mono-sesquioleate |
| Celluiose | Chlorinated insulator oil | Water |
| | Liquid paraffin or hydraulic oil or dibutyl sebacate or oleic acid or chlorotoluene or silicone oil . | Aqueous ammonium chloride and other electrolytes |
| Clays-diatomite, kaolinite, | Kerosene, plus 1% poly(isobutene) | Water |
| montmorillonite, vermiculite | Vaseline oil | Water |
| polygorskite | Hydrocarbons | Water |
| | Transformer oil | Diethylamine |
| | Lubricating oil | Water |
| Copper phthalo-cyanine | Paraffin grease or silicon oil | None |
| Gelatine | Transformer oil or olive oil or mineral oil | |
| Gypsum | Transformer oil or olive oil or mineral oil | |
| Ion exchange resins-strong and weak, acid and base, but otherwise unspecified | Di-n-butylphthalate or di-n-octylphthalate or di-n-decylphthalate or di-isodecylphthalate or tri-n-octyl trimeilitate or tri-2-ethylhexyl trimellitate or tri-isodecyl trimeilitate or tri-cresyl phosphate | Water |
| Iron(II) oxide | Petroleum fractions or dibutyi sebacate or di-2-ethylhexyl adipate | Water and surfactant |
| Iron(III) oxide | Petroleum fractions or dibutyl sebacate or di-2-ethylhexyi adipate | Water and surfactant |
| Lime | Transformer oil or olive oil or mineral oil | |
| Pentaerythritol | Mineral oil or p-exylene or poly(p-phenylmethyl siloxane) | Water and glycerol oleates |
| Phenol-formaldehyde type ion exchante resins based on resorcinol or z-resorcylic acid or 1,5 dihydroxy naphthalene or 2,2',4,4'-tetrahydroxy benzophenone-as lithium, sodium, potassium or guanidinium salts | Brominated diphenyl methanes | Water |
| Phthalocyanine | Silicon oil | None |
| Piezo-ceramic powder (unspecified) | Mineral oil or p-xylene | Water and glycerol oleates |
| Poly(acene-quinone radicals) based on anthracene or naphthalene or terphenyl or ferrocene or pyrene or phenanthrene | Chlorinated hydrocarbons or liquid paraffin/paraffin grease or silicone oils | None |
| Poly(acrylic acid)cross linked with divinyl benzene - as lithium salt | Chlorinated hydrocarbons or fluorolube FS-5 | Water |
| Poly(methacrylic acid) as lithium salt | Chlorinated hydrocarbons or fluorolube FS-5 Dipolarhalogenated aromatics or penta-chlorophenyl phenyl ether | Water Water |
| Poly(methacrylic acid) cross-linked with divinyl benzene-lithium or guanidium or mixed lithium/chromium salt | Chlorinated hydrocarbons or fluorolube FS-5 | Water |
| Poly(vinyl alcohol) | Hydrocarbons | Water |
| Silica | Kerosene or dibutyl sebacate | Water and soaps, sorbitol or fatty acid esters |
| | Naphthenic oils | Non-ionic surfactant |
| | Kerosene plus 1% poly(iso butene) | Water |
| | Hydrocarbons | Water |
| | Cetane | Diethylamine |
| | Mineral oil or xylene or silicone oil | Water and glycerol oleates |
| | Petroleum distillate or transformer oil or silicone oil | Water and water/glycerol and surfactant |
| Sodium carboxymethyl cellulose | Paraffin or silicone oils | Water |
| Sodium carboxymethyl dextran | Polychlorinated biphenyls or poly(tri-fluoroinylchloride) or o-dichlorobenzene or p-chlorotoluene or xylene or mixtures of the above | Water and sorbitan mono-oleate or sorbitan |
| Starch (flour) | Mineral or transformer oil olive oil Petroleum spirit or transformer oil | Water and sorbitan oleate or laureate |
| | Hydrocarbons, Vaseline oil | Water |
| Stone | Transformer oil or olive oil or mineral oil | |
| Sulphopropyl dextran | Polychlorinated biphenyls or poly(tri-fluorovinyl chloride) or | Water and sorbitan mono-oleate or |

TABLE 1-continued

| | The composition of ER-active fluid dispersions | |
|---|---|---|
| Dispersed Phase | Dispersant | Additive |
| | o-dicholorobenzene or xylene or mixtures of the above | sorbitan mono-sesquioleate |
| Tin(II) oxide | Petroleum fractions or dibutyl sebacate or di-2-ethylhexyl adipate | Water and a surfactant |
| Titanium dioxide | White spirit-vaseline mixture | Glycarol oleate plus a low molecular weight polymide or triethanol-amine |
| | Minerals oils or p-xylene or poly-(phenylmethylsiloxane) White spirit-alkyd resin mixture | Water and glycerol oleate |

The pumped fluid may consist of, for example, a liquid, a gas or gases, a liquid which contains a dissolved gas or gases, a mixture of gas and liquid, gas and suspended solids, a mixture of gas, liquid and suspended solids, or a biological fluid such as blood.

The electrical control 34 may be any suitable electronic and electrical apparatus designed to provide appropriately conditioned electrical power to drive the unidirectional pump 1 through multi-conductor electrical connections and to provide appropriate and properly programmed energizing voltage potential at typically low power levels to activate the electrorheological valves 24, 26, 30 and 32 through multiconductor electrical connectors. The electrical control 34 may incorporate batteries as an energy source, means for converting externally supplied power, means for sensing the condition of various components of the present invention, and means for controlling the present invention in compliance with a preprogrammed strategy. The electrical control 34 may contain means for energizing transducers and means of utilizing the signals from the transducers in the control of the present invention.

In the operation of the present invention as described with reference to FIG. 1, there are three possible modes of fixed amplitude fluid pumping, a different mode being shown in each of FIGS. 6,7 and 8.

In FIGS. 6 to 8, similar parts to those shown in FIG. 1 are designated by the same reference numerals and the previous description is relied upon to describe them.

In FIGS. 6 to 8, the fluid pressure transmitting devices 12 and 46 are diaphragms, and the first and second cavities 14, 16 and 48, 50 respectively are facing cavities.

FIG. 6 shows the operation with the valves 24 and 32 open and the valves 26 and 30 closed.

FIG. 7 shows the operation with the valves 26 and 30 open and the valves 24 and 32 closed.

FIG. 8 shows a different mode of operation to those previously described. In FIG. 8, with electrorheological valves 24 and 26 de-energized and thus open and electrorheological valves 30 and 32 energized and thus closed, electrorheological fluid from the outlet 2 of the pump 1 flows only through the first return loop 6 to the inlet 4 of the pump 1 without resulting in any substantial flow of electrorheological fluid or pumped secondary fluid into or out of the cavities 14 and 16. Further, with electrorheological valves 30 and 32 de-energized and thus open and electrorheological valves 24 and 26 energized and thus closed, electrorheological fluid from the outlet of the pump 1 flows only through the second return loop 40 to the inlet 4 of the pump 1 without resulting in any substantial flow of electrorheological fluid or pumped secondary fluid into or out of the cavities 48 and 50. Further with all of the electrorheological valves 24, 26, 30 and 32 de-energized and thus open the flow of electrorheological fluid from the outlet 2 of pump may simultaneously flow through both of the return loops 6 and 40 without any displacement of the diaphragms 12 or 46 occurring.

When the unidirectional pump 1 is a pump based on the conversion of fluid dynamic pressure to fluid static pressure, such as those with a centrifugal or axial flow impeller having an output flow which can be completely blocked without damage to the pump 1, the electrorheological valves 24, 26, 30 and 32 may be energized and thus closed, as described with reference to FIG. 8, so as to block the flow of electrorheological fluid from the outlet 2 of the pump 1 and thus to and from the cavities 14 and 48. It will be appreciated that the above described mode of operation is preferably performed using an impeller pump because it may not be possible to do this using any positive displacement type of pumps without an appropriate relief valve and return flow circuit from the pump outlet 2 to the pump inlet 4 since such pumps may be damaged by excessive back pressure at the pump outlet 2.

FIG. 9 shows an example of the operation of the system shown in FIGS. 6 to 8, with the maximum secondary fluid output flow rate when operating alternately in the modes described with reference to FIGS. 6 and 7. In FIG. 9, the output flow rate of the secondary fluid is shown in curve 112 as the secondary fluid pumped from the second cavity 50 as described with reference to FIG. 6. The output flow rate of the secondary fluid is shown as curve 114 as the secondary fluid pumped from the cavity 16 as described with reference to FIG. 7. It can be clearly seen that flow from the present invention may be substantially constant except for brief periods shown at 116 where the outlet flow is changed from the fluid pumping mode described with reference to FIG. 6 and to the fluid pumping mode described with reference to FIG. 7 or vice versa. The slope of the curves 112 and 114 at 118 and 120 respectively is dependent upon the response time of the electrorheological valves 24, 26, 30 and 32 and upon the inertia of the fluids within the components of the system.

Figure 10:
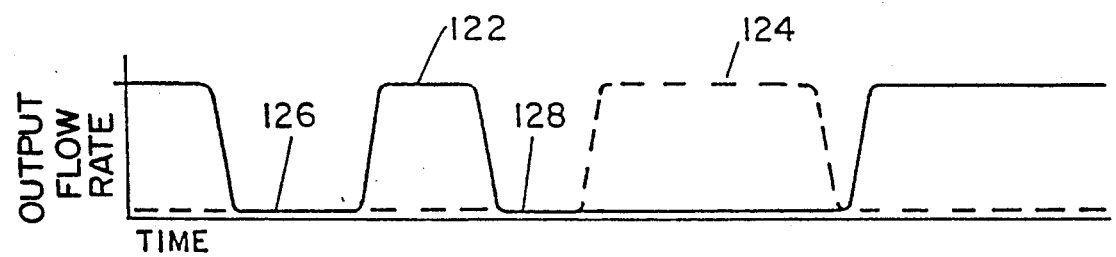

FIG. 10 shows how the maximum of the output fluid flow rate of the secondary fluid may be time modulated by appropriate combination of operation in the pumping modes described with reference to FIGS. 6,7 and 8. The output flow rate shown at 122 and 124 may be obtained by sequential operation in the modes described with reference to FIGS. 6 and 7 and the absence of output shown at 126 and 128 may be obtained by operation in either of the fully open or fully closed modes described with reference to FIG. 8.

FIG. 11 shows another way of operating the system shown in FIG. 6 and 7, wherein in the mode shown in FIG. 6, the electrorheological valve 30 is partially opened or modulated to allow some electrorheologic fluid to return to the pump inlet 4, thus modulating the flow of electrorheological fluid into the first cavity 48 and accordingly modulating the flow of secondary fluid out of the second cavity 50 as is shown by curve 130. Such operation can also be accomplished by modulating electrorheological valve 26 to allow some of the electrorheological fluid to flow from the pump outlet 2 to the pump inlet 4, thus modulating the flow of electrorheological fluid to the first cavity 14 and accordingly modulating the flow of pumped secondary fluid out of the second cavity 16 as is shown by curve 132 of FIG. 11. Similarly, when operating the present invention as described with reference to FIG. 7, the output flow of the pumped secondary fluid can be modulated by modulating the flow of electrorheological fluid through electrorheological valves 24 or 32.

In FIG. 12, similar parts to those shown in FIGS. 1 and 6 to 8 are designated by the same reference numerals and the previous description is relied upon to describe them.

FIG. 12 shows an embodiment of the present invention which can produce a substantially continuous or modulated output flow of secondary fluid. In FIG. 12, the primary fluid actuated, secondary fluid propelling devices 8 and 42 are arranged with their first cavities, 14 and 48 respectively, connected in series flow in the return loops 6 and 40 respectively, and are separated from the second cavities 16 and 50 by flexible diaphragms forming the fluid pressure transmitting devices 12 and 46. The casing 10 has an inlet 134 and outlet 136 communicating with the first cavity 14. The casing 44 has an inlet 138 and outlet 140 communicating with the first cavity 48. The pump comprises a centrifugal pump driven by a directly coupled electric motor 141 which is electrically interconnected to the control 34. The electrorheological valves 24, 26, 30 and 32 are similar in construction to each other and each is shown with two passages, such as passages 142 and 144, for the flow of electrorheological fluid therethrough and with electrodes, such as electrodes 146 and 148, which are on opposite sides of the passages 142 and 144 and are in contact with the electrorheological fluid, where the electrodes are connected to the electrical power supply and control 34 by electrical leads 150 and a common ground 152.

In operation, the electrorheological valves 24, 26, 30 and 32 are selectively closed by applying a D.C. or A.C. electrical voltage across the electrodes, such as electrodes 146 and 148, so as to create an electrical field between electrodes, such as electrodes 146 and electrodes 148, which affects the electrorheological fluid so as to reduce or stop the flow of the fluid through the valve, as has been previously described with reference to FIGS. 2, 3, 4 and 5. The removal of the voltage causes the valve to open allowing a free flow of electrorheological fluid through that valve. The check valves 38, 54, 60 and 62 are shown as conventional moving ball type valves.

Operation of the embodiment shown in FIG. 12 may be similar to that as described with reference to FIGS. 1, 6, 7 and 8 and similar outputs can be obtained as described with reference to FIGS. 9, 10 and 11.

In FIGS. 13 and 14, similar parts to those shown in FIG. 12 are designated by the same reference numerals and the previous description is relied upon to describe them. In FIG. 13, central portions of the diaphragms 12 and 46 are stiffened or reinforced by, for example, rigid plates 153 and 154 which are mechanically coupled to the ends of connecting rod 155 by means of bolts 156. The casings 10 and 44 are rigidly located relative to each other by means of a supporting structure (not shown) and each of the casings 10 and 44 contains a fluid tight slidable seal 157 which allows the connecting rod 155 to slide freely through the walls of the casings 10 and 44. The fluid pressure transmitting device 12 and 46 are arranged in a similar system to any of those shown in FIGS. 1, 6 to 8, and 12.

The operation of the embodiment shown in FIG. 13 is similar to that described with reference to FIGS. 1, 6, 7, 8 and 12 except that the diaphragms 12 and 46 are displaced in a synchronous manner because of their interconnection by the connecting rod 155. In this embodiment, while the movement of the diaphragms is similar to that in apparatus described by Credle in U.S. Pat. No. 4,682,937, dated Jul. 28, 1987 and No. 4,634,350, dated Jan. 6, 1987; Manchant in U.S. Pat. No. 4,624,628, dated Nov. 25, 1986; Santefort in U.S. Pat. No. 4,597,721, dated Jul. 1, 1986; Bazen in U.S. Pat. No. 4,566,867, dated Jan. 28, 1986; Rutenberg in U.S. Pat. No. 4,548,551 dated Oct. 22, 1985; and in numerous other patents, the actuation of them is novel in view of the novel arrangement of sequentially actuating them.

In FIG. 14, the outlet pipe 56 is connected to an inlet 160 of a secondary fluid processing apparatus 162, and the inlet pipe 52 is connected to an outlet 166 from the processing apparatus 162. A throttle connection 169 may be provided to allow excess secondary fluid to by-pass the processing apparatus 162.

This apparatus may be provided as a modification of the apparatus shown in FIGS. 1, 6 to 8, 12 and 13.

The processing apparatus 162 may be any known apparatus for modifying the pumped fluid by chemical, thermal, electrical or mechanical means or by the addition or subtraction in any manner to or from the secondary fluid or any combination thereof. By way of example, the processing apparatus 162 may involve the heating or cooling of the secondary fluid and, in the particular case of the use of the present invention as a blood pump, or as an artificial heart, the processing apparatus 162 may consist of biological lungs or of artificial lungs for the removal of carbon dioxide and for the oxygenation of the secondary fluid in the form of blood.

It will be appreciated that where the process of the processing apparatus 162 involves a change in the volume of the secondary fluid between the second cavity 16 within casing 10 of propelling device 8 and the second cavity 50 within casing 44 of propelling device 42, the throttle connection 169 may be required between the cavity 16, the outlet pipe 56 or the inlet 160 to the process apparatus 162 and the cavity 50, the inlet pipe 52 or the outlet 166 of the process apparatus 162 or in any combination thereof. The throttle connection 169 contains within its length a fluid flow constriction 170 so that the resistance to secondary fluid flow through the throttle connection 169 is significantly greater than the flow resistance through the process apparatus 162, the pipes 52, 56, 164, 168 and valves 54 and 60. The throttle connection 169 will allow for some bypass flow of the secondary fluid around the said process apparatus 162 in a direction appropriate to accommodate any change in pumped fluid volume.

In FIGS. 15 to 18, similar parts to those shown in FIGS. 1, 6 to 8, 12 and 14 are designated by the same reference numerals and the previous description is relied upon to describe them.

In FIG. 15 to 18 there is shown an implantable artificial heart pump where the components are designed, arranged and shaped to form a relatively flat and compact package for the purpose of anatomical fit. FIG. 15 shows the front view of the heart pump embodiment partially sectioned with respect to the pump 1, which in this embodiment is shown as a centrifugal pump, the pump outlet comprises a fluid conduit 2 which is in part a flow diffuser for the conversion of fluid dynamic pressure to fluid static pressure of the high velocity flow from the pump 1. The pump inlet comprises a fluid conduit 4, and the pumped fluid inlet conduits 40 and the secondary fluid inlet and outlet conduits 36, 56, 138 and 140 are shaped for a heart pump configuration. In FIG. 15 and 17, the second cavity 16 within casing 10 of fluid propelling device 8 is designated as the right ventricle of the heart pump and the second cavity 50 within casing 44 of fluid propelling device 42 is designated as the left ventricle of the heart pump with respect to their respective replacement functions for the natural heart. FIG. 16 shows a sectional view of the electrorheological valve 24. FIG. 17 shows a top view of the heart pump embodiment in direction A—A of FIG. 15. FIG. 18 shows an end view of the heart pump embodiment in direction B—B of FIG. 15.

In operation of the heart pump embodiment of the present invention shown in FIGS. 15, 16, 17 and 18, with the electrorheological valves 24 and 32 open and the electrorheological valves 26 and 30 closed, the unidirectional pump 1 pumps electrorheological fluid from the first cavity 14 within casing 10 of fluid propelling device 8, through fluid conduit 20, electrorheological valve 24 and fluid inlet 4, so as to displace the diaphragm 12 of the casing 10 and accordingly so as to accept a flow of blood from the venous system of the body to flow into the second cavity 16, or right ventricle, through fluid conduit 36, and check valve 38 which provides for the function of the right atrium outlet tricuspid valve of the natural heart. Simultaneously, the unidirectional pump 1 pumps electrorheological fluid to the first cavity 48 of casing 44 of fluid propelling device 42, or left ventricle, from fluid outlet 2 through electrorheological valve 32 and fluid conduit 40, so as to displace the diaphragm 46 of the casing 44 and deliver a flow of blood, pressurized at substantially the aorta blood pressure, to the arterial system of the body via the aortic artery from the second cavity 50 or left ventricle, through fluid conduit 140 and check valve 62 which provides for the function of the aortic valve of the natural heart.

In operation of the heart pump embodiment of the present invention shown in FIGS. 15, 16, 17 and 18, with the electrorheological valves 24 and 32 closed and the electrorheological valves 26 and 30 open, the unidirectional pump 1 pumps electrorheological fluid from the first cavity 14 within casing 10 of fluid propelling device 8, or right ventricle, through the electrorheological valve 26 and the fluid conduit 20, to the fluid inlet 4, so as to displace the diaphragm 12 of the casing 10 of fluid propelling device 8 and deliver a flow of blood, pressurized to substantially the body pulmonary system input blood pressure, from the second cavity 16 within casing 10 of fluid propelling device 8, or right ventricle, through the fluid conduit 56 and check valve 60, which provides for the function of the pulmonary valve of the natural heart, to the lungs via the pulmonary artery of the body. Simultaneously, the unidirectional pump 1 pumps electrorheological fluid from the first cavity 48 within casing 44 of fluid propelling device 42, or left ventricle, through fluid conduit 40 and electrorheological valve 30 so as to displace the diaphragm 46 of the casing 44 of fluid propelling device 42 and accordingly so as to accept a flow of blood from the lungs via the pulmonary veins to flow into the second cavity 50 within casing 44 of device 42, or left ventricle, through the fluid conduit 138 and check valve 54, which provides for the function of the left atrium outlet mitral valve of the natural heart.

The operation of the heart pump embodiment of the present invention, that is alternately having electrorheological valves 26 and 30 open and valves 24 and 32 closed or having electrorheological valves 26 and 30 closed and valves 24 and 32 open, is, as described above, regulated by the electrical control unit 34 (shown in FIG. 1) which, while supplying power to the unidirectional pump, energizes the said electrorheological valves in appropriately timed sequenced combinations in response to transducers (not shown) which sense one or more physiological phenomena of the body such as blood pressure or heart electrical cardiac function or one or more physical condition of the present invention such as pump speed, electrorheological fluid or blood flow rate, displacement chamber or fluid flow conduit pressure or such other conditions or input signals as may be used to control this embodiment of the present invention.

It has been noted by Jarvik in U.S. Pat. No. 4,173,796 that in a closed hydraulic drive system for an artificial heart, such as that described in the said artificial heart embodiment of the present invention, the blood through flow rate of the left and the right ventricles are not necessarily equal. The Jarvik patent indicates that this blood flow unbalance may be accommodated by providing a left ventricle cavity casing which is structurally stiffer than the right ventricle cavity casing and/or by providing a right ventricle cavity inflow valve having a greater reverse flow capacity than the left ventricle cavity inflow valve so as to provide blood volume flow rate compliance with the physiological demand. A similar blood flow unbalance accommodation could also be incorporated into the heart pump embodiment of the present invention.

A further embodiment of the present invention in the form of an implantable artificial heart pump is shown in FIG. 19. In FIG. 19 similar parts to those shown in FIGS. 1, 6 to 8 and 12 to 18 are designated by the same reference numerals and the previous description is relied upon to describe them. In the embodiment shown in FIG. 19, the unidirectional pump 1 is shown as an axial flow pump driven by electric motor 141. The operation of the heart pump embodiment shown in FIG. 19 is similar to the embodiment described with reference to FIGS. 15, 16, 17 and 18.

It will be apparent from the description of yet further embodiments of the present invention that the first fluid propelling device 8 containing the second cavity 16, or right ventricle, the second fluid propelling device 42 containing the second cavity 50, or left ventricle and the unidirectional pump 1 may each be located at some distance from one another or may be located immediately adjacent to each other to accommodate anatomical fit in the body by using appropriately longer or shorter electrorheological fluid conduits 20 and 40 and pumped fluid conduits 36, 56, 138 and 140.

In FIGS. 20 and 21, similar parts to those shown in FIGS. 1, 6 to 8 and 12 to 19 are designated by the same reference numerals and the previous description is relied upon to describe them.

Yet a further embodiment of the present invention is an implantable artificial ventricle heart assist pump having an electrorheological fluid accumulator without the fluid displaced volume being compensated by another fluid. This embodiment is shown in FIGS. 20 and 21 where the apparatus components are shaped and arranged so as to form a relatively flat and distributed assembly for the purpose of anatomical fit. FIG. 20 shows a front view of portions of an uncompensated ventricle assist pump and FIG. 21 shows a side view of a variable displacement volume electrorheological fluid accumulator. It will be appreciated that the subassembly comprising unidirectional pump 1, fluid outlet 2, fluid inlet 4, interconnecting conduits 20 and 40 and electrorheological values 24, 26, 30 and 32 may be located in close proximity to casing 10 of the fluid propelling device 8 or to the casing 44 of fluid propelling device 42 or at any convenient location between the casings by means of appropriate arrangement of the fluid conduits 20 and 40 to accommodate anatomical fit in the body.

In FIG. 20, the second cavity 16 within casing 10 is, as previously stated, an assist device for the left ventricle of the heart assist pump with respect to its replacement function of the natural heart. With this left ventricle designation of cavity 16, the inlet conduit 36 to the assist pump is connected to the blood flow from the lungs and the outlet conduit 56 from the assist pump is connected to the body arterial system. It will be appreciated that this designation of cavity 16 as a heart left ventricle assist device may be altered to the designation as a heart right ventricle assist device where the inlet conduit 36 to the assist pump is connected to the body venous system and the outlet conduit 56 from the assist pump is connected to the body pulmonary artery.

The operation of the heart ventricle assist pump embodiment of the present invention as shown in FIGS. 20 and 21 is similar to that for the previously described heart pump embodiment as shown in FIGS. 15 to 19 with the exception that the first cavity 48 of the fluid propelling device 42 functions as an electrorheological fluid accumulator in that second cavity 50 of propelling device 42 and its casing portion is eliminated and the second cavity side of the diaphragm 46 is directly exposed to the ambient internal body pressure as shown in FIG. 21. It will be appreciated that the first cavity 48, when functioning as a fluid accumulator, could be comprised of a fluid container with nonrigid walls such a rubber sack and having appropriate interconnections to the electrorheological fluid inlet and outlet conduits 40.

Yet a further embodiment of the present invention is an implantable artificial ventricle heart assist pump having an electrorheological fluid accumulator with the fluid displaced volume being compensated by blood from the body blood stream. This embodiment is shown in FIGS. 22 and 23 where the apparatus components are shaped and arranged so as to form a relatively flat and distributed assembly for the purpose of anatomical fit.

In FIGS. 22 and 23, similar parts to those shown in FIGS. 1, 6 to 8 and 12 to 20 are designated by the same reference numerals and the previous description is relied upon to describe them.

FIGS. 22 and 23 show front and side views of portions of a heart ventricle assist pump embodiment with a blood volume compensated electrorheological fluid accumulator with the unidirectional pump 1 partially sectioned in FIG. 22 to reveal the heart pump configuration. The second cavity 16 within the casing 10 of fluid propelling device 8 is provided to function as the left ventricle with respect to natural heart function similarly as previously described for FIGS. 15 through 19.

Operation of the heart ventricle assist pump as shown in FIGS. 22 and 23 is similar to that for the previously described heart pump embodiment as shown in FIGS. 20 and 21 with the exception that the second fluid propelling device 42 not only functions as the electrorheological fluid accumulator with respect to its first cavity 48 within casing 44 but also is provided with the second cavity 50 which functions as a blood accumulator so as to compensate for the first cavity 48 electrorheological fluid volume displacement. When functioning as a left ventricle assist device, the blood inlet 36 to the second cavity 16 of device 8 is connected to the blood flow from the lungs (not shown), without imposition of a check valve therebetween and the blood outlet 56 from the second cavity 16 of the first propelling device 8 is directly interconnected via check valve 54 by means of blood conduit 175 to the inlet 138 to the second cavity 50 of the second propelling device 42 and the blood outlet 140 from the second cavity 50 is connected via check valve 62 to the body arterial system. When functioning as a right ventricle assist device, the blood inlet 36 is connected to the blood flow from the body venous system, without imposition of a check valve therebetween and the blood outlet 140 is connected to the body pulmonary arterial system.

It has been found that the performance characteristic requirements of the electrorheological fluids specifically for the heart pump embodiments of the present invention are more than adequately met by the experimentally determined characteristics of known electrorheological fluids. Specifically, the low pressure of the output pumped fluid required for the heart pump embodiments allows for the use of electrorheological fluids as have previously been described and having known characteristics, which do not require excessively high voltage for the operation of the electrorheological valves.

The implantation of the heart pump embodiment of the present invention within the substantially constant temperature heat sink of the body thoracic cavity, combined with the continuous circulation of the electrorheological fluid to the substantial and effective heat transfer surfaces of the heart pump apparatus which are exposed to the body heat sink, including the displacement chamber walls and diaphragm, ensures that the temperature of the electrorheological fluid will remain substantially constant at least during operation of the heart pump when implanted. Maintaining constant temperature of the electrorheological fluid is known to prevent degradation of the fluid performance from nominal design operating values. Such degradation is particularly notable with respect to electrorheological fluid electrical conductivity and accordingly to the power consumption of electrorheologic values which is directly related thereto. Many electrorheological fluids are known to typically be very temperature sensitive as described, for example, by Block and Kelly, Journal of Physics D; Applied Physics V 21 (1988) pp 1661-1667.

Further, continuous operation of the heart pumps of the present invention results in continuous pumping agitation of the electrorheological fluid which effectively prevents any substantial sedimentation of the dispersed phase of electrorheological fluids. Such sedimentation of electrorheological fluids in the absence of adequate agitation of the fluid is known to seriously degrade the electrorheological properties.

From the above descriptions it will be seen that;

1) The present invention differs from the apparatus described by Dexter in U.S. Pat. No. 3,405,728, dated Oct. 15, 1968, Stangroom in U.S. Pat. No. 4,342,334, dated Aug. 1, 1982, and Bullough et al in G.B. patent 1,511,658, dated May 24, 1978, in that the above referenced patents use a first electrorheological fluid and associated electrorheological valves to control the movement of an actuator or the spool of another valve device which, in turn, regulates the flow of a second fluid without the addition of any significant energy to the first fluid. In contrast, the present invention adds significant energy in the form of fluid pressure, flow or a combination thereof, to a first electrorheological fluid which transfers most of this energy to a second fluid which need not necessarily be an electrorheological fluid, 2) In Stangroom, a second fluid is used to pump, by means of energy transfer, a first electrorheological fluid by adding energy in the form of fluid pressure, flow or a combination thereof to the first fluid which, in turn, controls a hydraulic servo valve, in contrast to the present invention wherein a first electrorheological fluid is used to pump, by means of energy transfer, a second fluid by adding energy in the form of fluid pressure, flow or a combination thereof to the first fluid, 3) The present invention differs from the apparatus described by Shulman et al in U.S. Pat. No. 731,045, dated Apr. 30, 1980, in that the referenced patent provides for the transfer of energy in the form of fluid pressure, flow or a combination thereof from a first electrorheological fluid to a second fluid, which is not necessarily an electrorheological fluid, by means of a displacement chamber wherein the pumping by a hydopulsator of the first electrorheological fluid to the displacement chamber is cyclic and can not be made continuous and the electrorheological fluid circuit is shaped to accommodate such a discontinuous pumping means. In contrast, in the present invention the pumping of the electrorheological fluid is continuous. Also, Shulman et al shows a common conduit for the flow of electrorheological fluid to and from a displacement chamber in contrast with the present invention where separate conduits are provided for the flow of electrorheological fluid to and from a fluid propelling device, 4) The present invention, when used as a heart pump or heart assist pump device to pump a second fluid which is blood, uses a first electrorheological fluid and associated electrorheological valves combined with a unidirectional first fluid pump which runs at a substantially constant speed within any given heart pump cycle, in contrast with other electrohydraulic powered heart pump devices such as those described by Robinson et al in U.S. Pat. Nos. 4,369,530, dated Jan. 25, 1983; 4,376,312, dated Mar. 15, 1983; 4,381,567, dated May 3, 1983; 4,389,737, dated June 28, 1983 and 4,397,049, dated Aug. 9, 1983; by Jarvik in U.S. Pat. No. 4,173,796, dated Nov. 13, 1979; and by Goldschmied in U.S. Pat. No. 3,568,214, dated Mar. 9, 1971.

We claim:

1. A primary fluid actuated, secondary fluid propelling system, (characterized in that it comprises) comprising:
   a) a unidirectional pump for, in operation, being flooded with electrorheological fluid, and having an outlet and an inlet,
   b) a return loop connected for, in operation, being filled with electrorheological fluid and conveying electrorheological primary fluid from the pump outlet to the pump inlet,
   c) a primary fluid actuated, secondary fluid propelling device comprising a casing and a fluid pressure transmitting device dividing the casing interior in a fluid tight manner into a first cavity and a second cavity, the first cavity being, in operation, filled with electrorheological fluid, and being connected to an intermediate, lengthwise extending portion of the return loop for, in operation, receiving therefrom pressurized, electrorheological primary fluid and then being at least partially evacuated of electrorheological primary fluid thereby, and the second cavity (for, in operation, propelling secondary fluid from a source thereof) having an inlet and an outlet connected to respective check valves arranged such that as electrorheological fluid is at least partially evacuated from said first cavity, secondary fluid is drawn into said second cavity through the inlet thereof, and as said first cavity is filled with electrorheological fluid, said second fluid is propelled out of said second cavity through the outlet thereof due to the action of said pressure transmitting device under the influence of the electrorheological fluid in the first cavity,
   d) an upstream electrorheological valve in an upstream portion of the return loop to the connection to the first cavity,
   e) a downstream electrorheological valve in a downstream portion of the return loop from the connection to the first cavity,
   f) a rheological fluid supplying/receiving means, comprising;
      i) an electrorheological supply valve for, in operation, supplying and receiving electrorheological fluid to and from the pump, and
      ii) an electrorheological return valve for receiving electrorheological fluid from the pump outlet, and
   g) an electrical control for energizing the electrorheological valves for, in operation, simultaneously allowing the flow of electrorheological fluid through the upstream (downstream) valve and the supply valve, while substantially inhibiting the flow of electrorheological fluid through the (upstream) downstream valve and the return valve, and vice versa.

2. A system according to claim 1, (characterized in that) wherein the return loop is a first return loop, the return loop electrorheological valves are first return loop electrorheological valves, the fluid propelling device is a first fluid propelling device, and the supplying-/receiving means of rheological fluid further comprises;
   a) a second return loop, in operation, filled with electrorheological fluid, and containing said electrorheological supply and return valves and forming the connections between them and the pump inlet and outlet, and b) a second fluid propelling device comprising a casing, and a fluid pressure transmitting device dividing the casing interior in a fluid tight manner into a first cavity, in operation, filled with electrorheological fluid, and connected to an intermediate, lengthwise extending portion of the second return loop having the return valve (downstream) upstream and the supply valve (upstream) downstream, and a second cavity (for, in operation, propelling secondary fluid from a source thereof) having an inlet and an outlet connected to respective check valves arranged such that as electrorheological fluid is at least partially evacuated from said first cavity of said second fluid propelling device, secondary fluid is drawn into said second cavity of said second fluid propelling device through the inlet thereof, and as said first cavity of said second fluid propelling device is filled with electrorheological fluid, said secondary fluid is propelled out of said second cavity of said second fluid propelling device through the outlet thereof due to the action of said pressure transmitting device under the influence of the electrorheological fluid in the first cavity of said second fluid propelling device, c) said first cavities of said first and second propelling devices thereby being arranged in opposition such that as one cavity is filled with electrorheological fluid the other is evacuated, and vice versa, and said second cavities of said first and second propelling devices thereby being similarly arranged such that is secondary fluid is being drawn into one said second cavities through the inlet thereof it is being propelled out of the outlet and the other second cavity and, vice versa.

3. A system according to claim 2, characterized in that the intermediate lengthwise extending portions of the first and second return loops are T-junctions with the cross-bars of each T connected to the electrorheological valves, and the trunks of each T connected to fluid pressure transmitting devices.

4. A system according to claim 2, characterized in that the fluid pressure transmitting devices each comprise a flexible diaphragm.

5. A system according to claim 4, characterized in that central portions of the diaphragms are stiffened, and a connecting rod is provided connecting the diaphragms and extending through the second cavities and the walls of the casings in a slidable, fluid tight manner.

6. A system according to claim 2, characterized in that it further comprises a throttle connection between the second cavities.

7. A system according to claim 1, characterized in that the unidirectional pump is an impeller pump.

8. A system according to claim 1, characterized in that it is shaped for an anatomical fit for the purpose of an implantable artificial heart pump.

9. A system according to claim 1, characterized in that it is shaped for an anatomical fit for the purpose of an implantable artificial ventricle heart assist pump, and the electrorheological fluid supplying/receiving means further comprises a casing connected in series flow between the supply and return valves, and for, in operation, placement in the body cavity, at least a portion of the casing being flexible for, in operation, transmitting body fluid pressure within the body cavity.

10. A system according to claim 1, characterized in that it is shaped for an anatomical fit for the purpose of an implantable artificial ventricle heart assist pump, and the electrorheological fluid supplying/receiving means further comprises a substantially rigid casing and, a fluid pressure transmitting device dividing the casing interior into two cavities, one cavity within the casing fluid connected in series flow between the electrorheological fluid supply and return valves, and the other cavity within the casing being for in operation connection in series flow to the body blood stream.

* * * * *